(12) United States Patent
Arayama et al.

(10) Patent No.: US 9,320,658 B2
(45) Date of Patent: Apr. 26, 2016

(54) DISPOSABLE DIAPER

(75) Inventors: Takaya Arayama, Kagawa (JP);
Hirotomo Mukai, Kagawa (JP)

(73) Assignee: UNICHARM CORPORATION, Ehime-Ken (JP)

( * ) Notice: Subject to any disclaimer, the term of this patent is extended or adjusted under 35 U.S.C. 154(b) by 272 days.

(21) Appl. No.: 14/003,725

(22) PCT Filed: Dec. 20, 2011

(86) PCT No.: PCT/JP2011/079473
§ 371 (c)(1),
(2), (4) Date: Nov. 11, 2013

(87) PCT Pub. No.: WO2012/120748
PCT Pub. Date: Sep. 13, 2012

(65) Prior Publication Data
US 2014/0058348 A1  Feb. 27, 2014

(30) Foreign Application Priority Data

Mar. 8, 2011  (JP) ................................ 2011-050869

(51) Int. Cl.
*A61F 13/15* (2006.01)
*A61F 13/49* (2006.01)
(Continued)

(52) U.S. Cl.
CPC ..... *A61F 13/49019* (2013.01); *A61F 13/49001* (2013.01); *A61F 13/4902* (2013.01);
(Continued)

(58) Field of Classification Search
CPC .................... A61F 13/15203; A61F 13/49017; A61F 13/4704; A61F 13/49019; A61F 2013/49084; A61F 2013/4568; A61F 2013/4575; A61F 2013/4543; A61F 2013/4512; A61F 2013/49041; A61F 2013/530437

USPC ............. 604/385.24, 385.25, 385.26, 385.27, 604/385.28, 385.29, 385.3
See application file for complete search history.

(56) References Cited

U.S. PATENT DOCUMENTS 6,689,115 B1    2/2004 Popp et al.
2003/0040732 A1 *  2/2003 Ishikawa ........... A61F 13/49017
604/385.29

(Continued)

FOREIGN PATENT DOCUMENTS

CN    1518909 A    8/2004
DE    102005030182 A1    1/2007

(Continued)

OTHER PUBLICATIONS

International Search Report and Written Opinion corresponding to PCT/JP2011/079473, dated Mar. 13, 2012.

(Continued)

*Primary Examiner* — Jacqueline Stephens
(74) *Attorney, Agent, or Firm* — Hauptman Ham, LLP

(57) ABSTRACT

A disposable wearing article includes an absorber having a crotch region that is in contact with a crotch portion of the wearer, and a back region arranged posterior to the crotch region and in contact with the hip portion of the wearer, and in the crotch region, a pair of curving means are provided along the crosswise direction so as to enable the absorber to curve in a convex shape in an inner direction, and outside the widthwise direction of the curving means, a pair of lifting units are provided along the crosswise direction so as to enable the absorber to be lifted up in an inner direction in the back region, and the back ends of the curving means are positioned anterior to the back ends of the lifting units.

16 Claims, 14 Drawing Sheets

(51) Int. Cl.
*A61F 13/535* (2006.01)
*A61F 13/494* (2006.01)
*A61F 13/47* (2006.01)
*A61F 13/45* (2006.01)
*A61F 13/53* (2006.01)

(52) U.S. Cl.
CPC ....... *A61F13/49017* (2013.01); *A61F 13/4946* (2013.01); *A61F 13/49406* (2013.01); *A61F 13/49426* (2013.01); *A61F 13/535* (2013.01); *A61F 13/15203* (2013.01); *A61F 13/4704* (2013.01); *A61F 2013/4512* (2013.01); *A61F 2013/4543* (2013.01); *A61F 2013/4568* (2013.01); *A61F 2013/4575* (2013.01); *A61F 2013/49041* (2013.01); *A61F 2013/49084* (2013.01); *A61F 2013/530437* (2013.01)

(56) References Cited

U.S. PATENT DOCUMENTS

| | | |
|---|---|---|
| 2006/0264859 A1 | 11/2006 | Tsuji et al. |
| 2008/0027406 A1 | 1/2008 | Shirai et al. |

FOREIGN PATENT DOCUMENTS

| | | |
|---|---|---|
| JP | 5-033630 B2 | 5/1993 |
| JP | 08-182703 A | 7/1996 |
| JP | 09-187477 A | 7/1997 |
| JP | 2004-505726 A | 2/2004 |
| JP | 2006-149749 A | 6/2006 |
| JP | 2006-346439 A | 12/2006 |
| JP | 2009-11378 A | 1/2009 |
| WO | 0213748 A2 | 2/2002 |

OTHER PUBLICATIONS

Extended European Search Report issued Oct. 14, 2014, corresponding to European patent application No. 11860505.4.
Office Action issued May 15, 2015, corresponding to Australian patent application No. 2011361634.
Office Action mailed Feb. 3, 2015, corresponding to Japanese patent application No. 2011-050869.
Office Action issued Aug. 5, 2014, corresponding to Chinese patent application No. 201180069047.8.

* cited by examiner

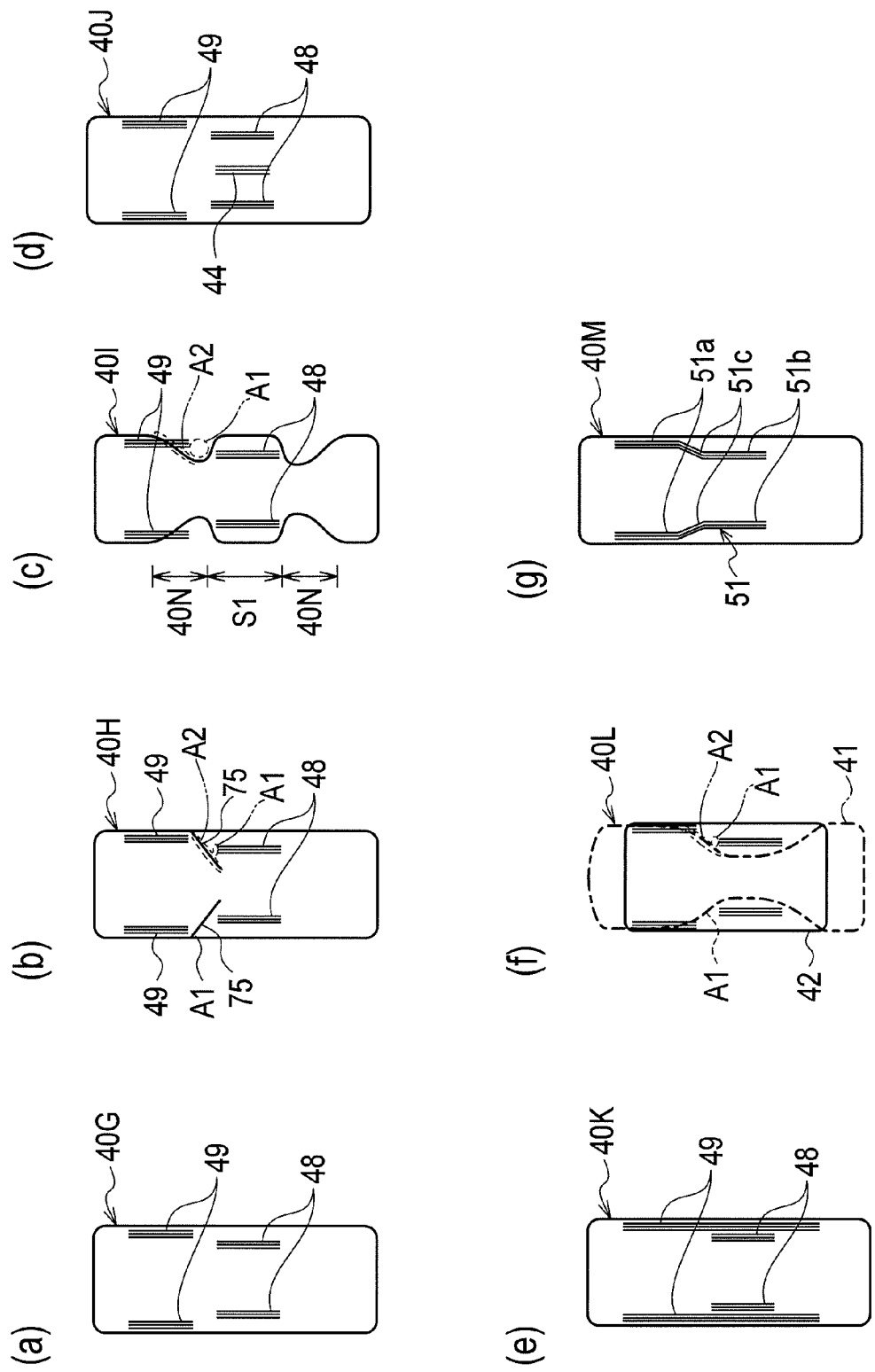

DISPOSABLE DIAPER

RELATED APPLICATIONS

The present application is a National Phase of International Application Number PCT/JP2011/079473, filed Dec. 20, 2011, and claims priority from Japanese Application Number 2011-050869, filed Mar. 8, 2011.

TECHNICAL FIELD

The present invention relates to a disposable wearing article having a curving means that enables an absorber to be curved.

BACKGROUND ART

In a disposable wearing article such as a pant-type diaper, in order to improve the comfort of the wearer when wearing the disposable article and to prevent leakage of bodily waste, various means have been devised. For example, a disposable wearing article having an elastic member in the form of a curving means that enables an absorber to be curved towards the wearer is known (for example, Patent Document 1).

Specifically, the disposable wearing article has a central absorber arranged in the center of the widthwise direction of the worn article, an elastic member arranged on both outer sides of the widthwise direction of the central absorber, and an outer absorber arranged outside the widthwise direction of the elastic materials. According to the disposable wearing article, because the portion in which the elastic members are arranged is deformed due to the elastic members so as to curve towards the wearer, the fitting is improved, and the comfort of the wearer when wearing the disposable article can be improved and the leakage of bodily waste can be prevented.

RELATED ART DOCUMENT

Patent Document

[Patent Document 1] Japanese Examined Patent Publication No. H5-33630 (Page 4, FIG. 1)

SUMMARY OF INVENTION

However, the aforementioned disposable wearing article has the following problems. An outer absorber is provided not only in the crotch region that is in contact with the crotch of the wearer, but also in the back region that is in contact with the hip portion, and is desired to be arranged in a curved shape along the outer shape of the body of the wearer. However, the elastic members are arranged not only in the crotch region but also in the back region. When the portion in which the elastic members are arranged is deformed due to the elastic members so as to curve towards the wearer, the outer absorber outside the widthwise direction from the elastic members cannot curve easily along the outer shape of the body. Particularly, in the proximity of the hip portion, because the outer shape of the hip portion is in the form of a curve, the absorber cannot curve easily along the outer shape of the body, which causes either a gap between the body of the wearer and the absorber or too close a contact, resulting in deterioration in comfort at the time of wearing and also leakage.

Therefore, an object of the present invention is to provide a disposable wearing article such as a pant-type diaper that can prevent deterioration in comfort at the time of wearing and the occurrence of leakage by improving the fitting in the proximity of the hip portion of the wearer.

An aspect of the present invention is summarized as a disposable wearing article comprising: an absorber (absorber 40) having a crosswise direction extending to a front of the body and a back of the body of a wearer, a widthwise direction (widthwise direction W) perpendicular to the crosswise direction, an inner direction (inner direction IN) facing the wearer, and an outer direction (outer direction OUT) facing the opposite side of the inner direction, and is configured such that the absorber has a crotch region (crotch region S1) that is in contact with a crotch portion of the wearer, a front region (front region S2) arranged anterior to the crotch region, and a back region (back region S3) arranged posterior to the crotch region and in contact with a hip portion of the wearer, said disposable wearing article, wherein in the crotch region, a pair of curving means (first elastic materials 48) are provided along the crosswise direction so as to enable the absorber to curve in a convex shape in the inner direction, outside the widthwise direction of the curving means, a pair of lifting units (second elastic materials 49) are provided along the crosswise direction so as to enable the absorber to be lifted up in the inner direction in the back region, and the back ends (back ends 48B) of the curving means are positioned anterior to the back ends (back ends 49B) of the lifting units.

BRIEF DESCRIPTION OF DRAWINGS

FIG. 14 are plan views each illustrating an absorber of the disposable diaper 1 according to a modification.

DESCRIPTION OF EMBODIMENTS

Figure 1:
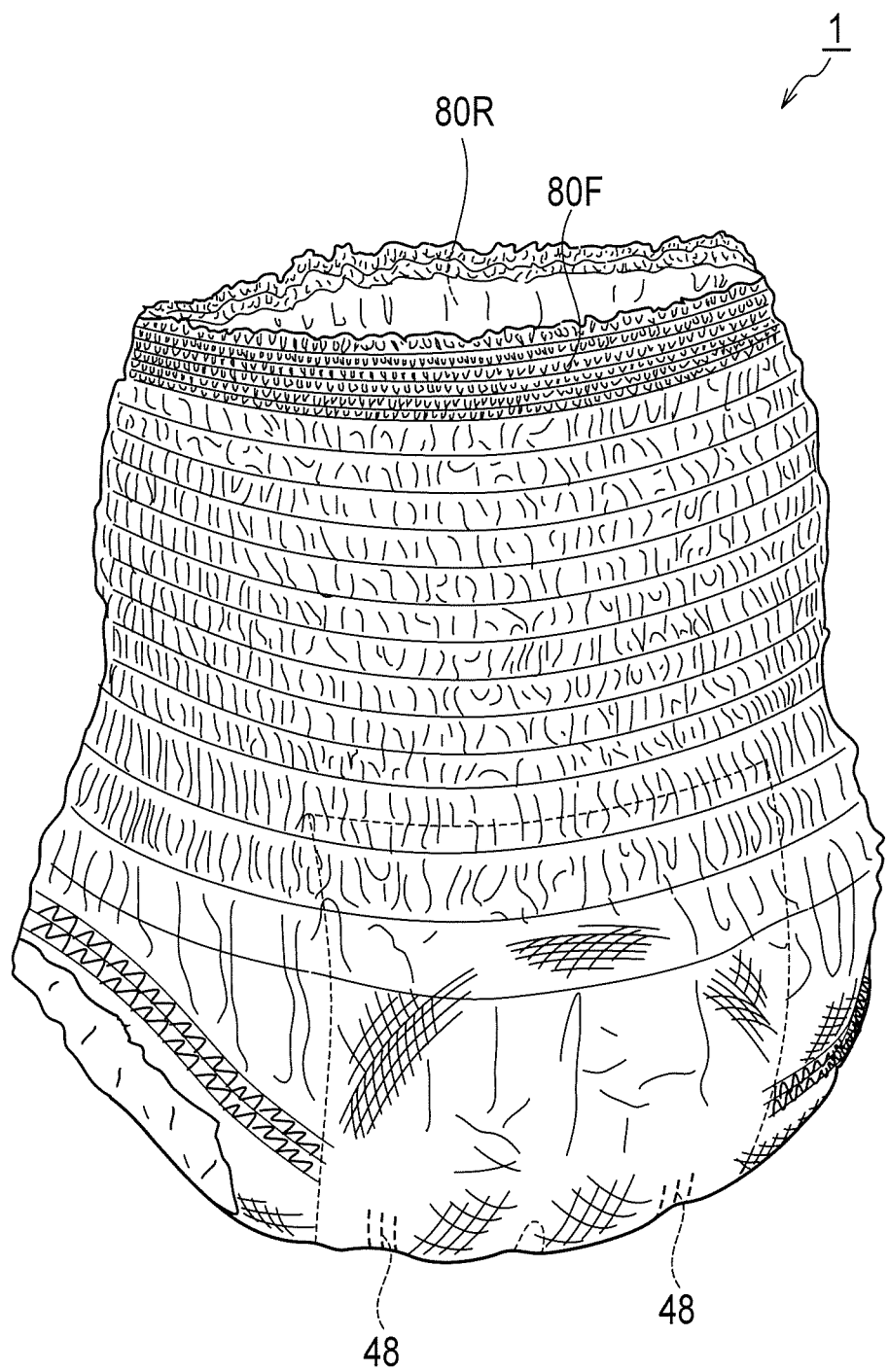
FIG. 1 is a simplified perspective schematic view of a disposable diaper 1 according to a first embodiment.

Next, an embodiment of a disposable diaper 1 according to the present invention is explained with reference to drawings. Specifically, a first embodiment and modifications are explained.

In the following description of the drawings, the same or similar reference numerals are used to designate the same or similar parts. It will be appreciated that the drawings are schematically shown and the ratio and the like of each dimension are different from the real ones.

Accordingly, specific dimensions should be determined in consideration of the explanation below. Moreover, among the drawings, the respective dimensional relations or ratios may differ.

First Embodiment

The disposable wearing article according to the present embodiment includes a pair of first curving means and a pair of lifting units, and the back ends of the first curving means are positioned anterior to the back ends of the lifting units.

(1) Entire Schematic Configuration of the Disposable Wearing Article

Figure 2:
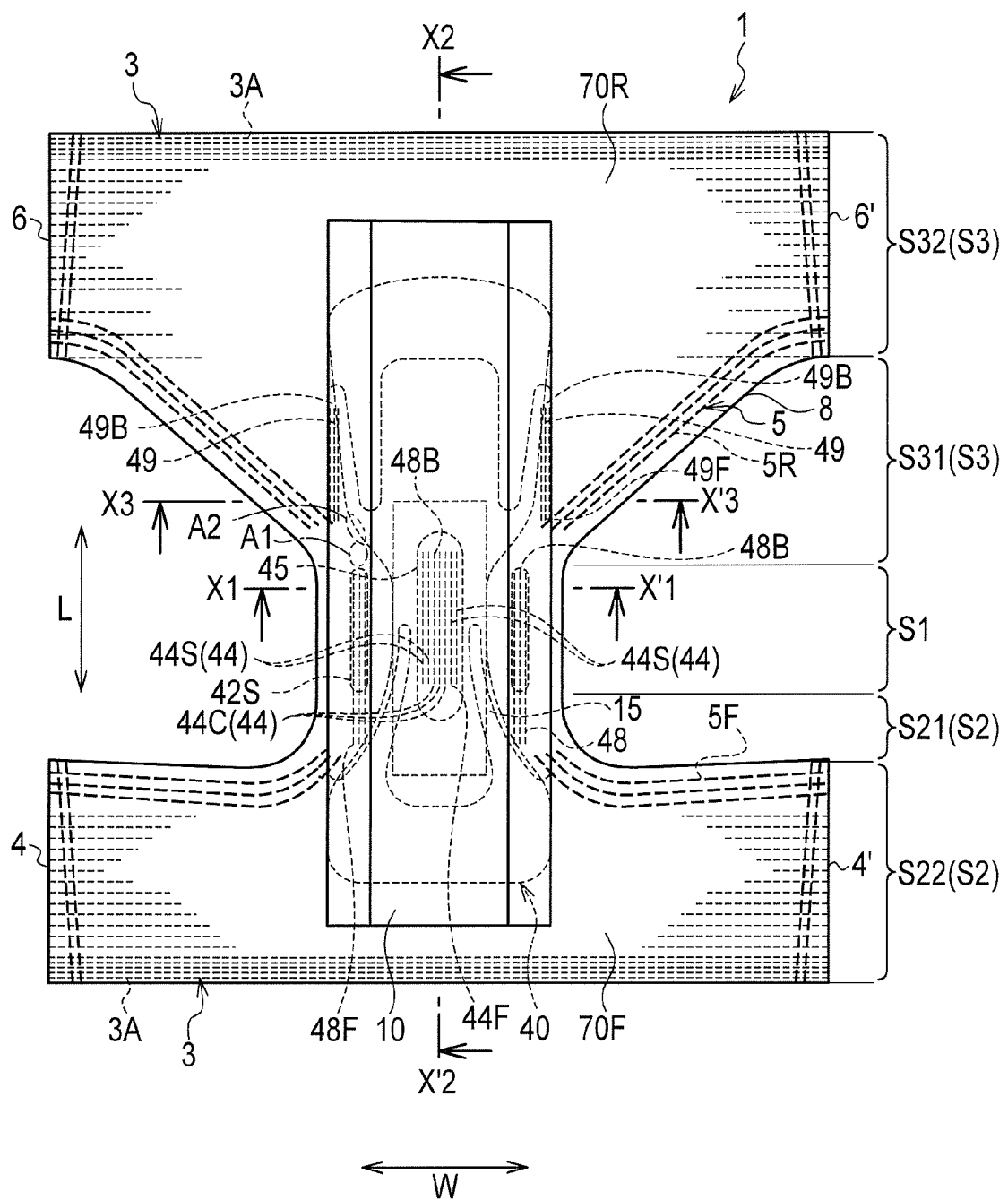
FIG. 2 is an exploded plan view of the disposable diaper 1 according to the first embodiment.
Figure 3:
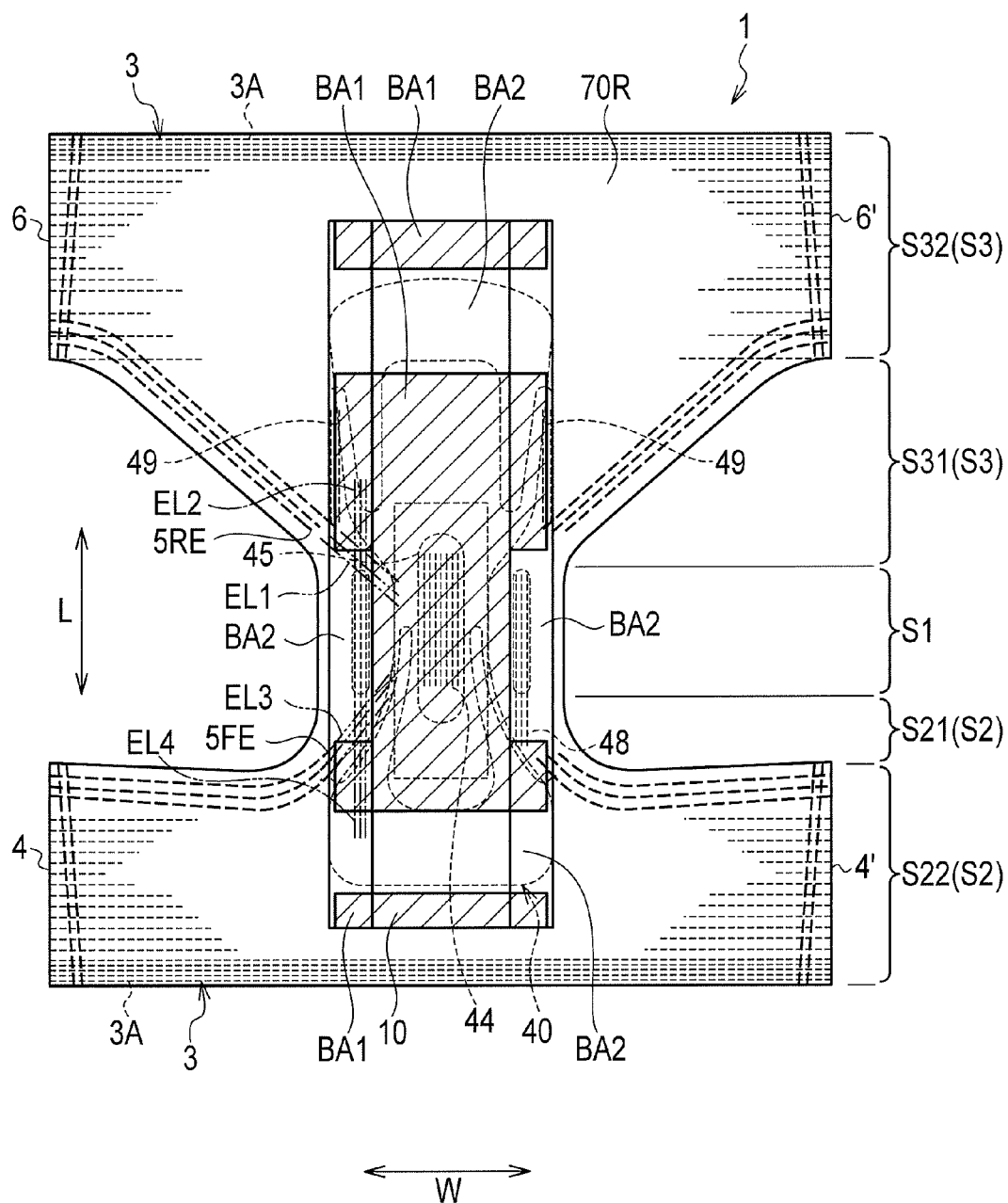
FIG. 3 is an exploded plan view of the disposable diaper 1 according to the first embodiment.
Figure 4:
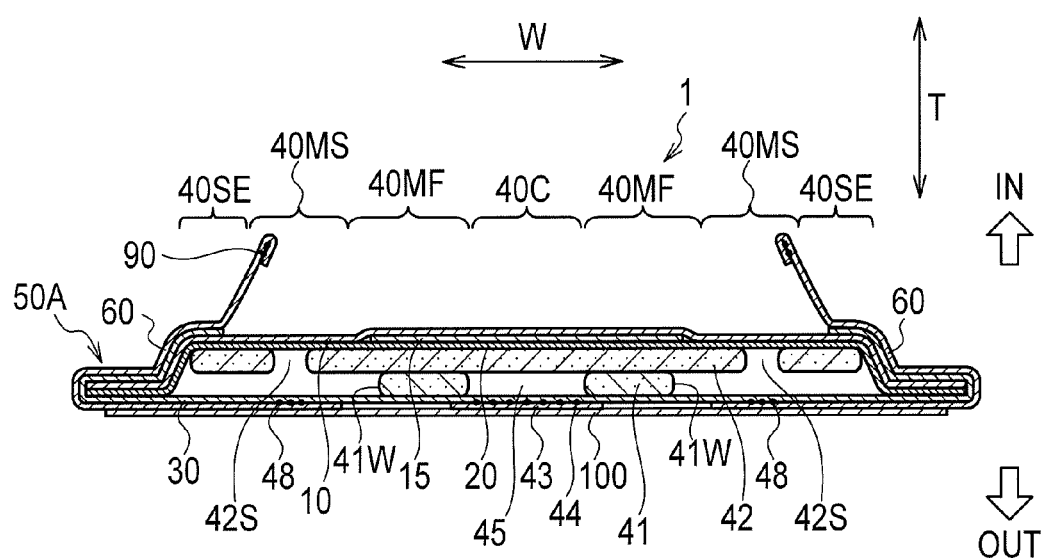
FIG. 4 is a widthwise cross-sectional view of the disposable diaper 1 along the X1-X'1 line shown in FIG. 2.
Figure 5:
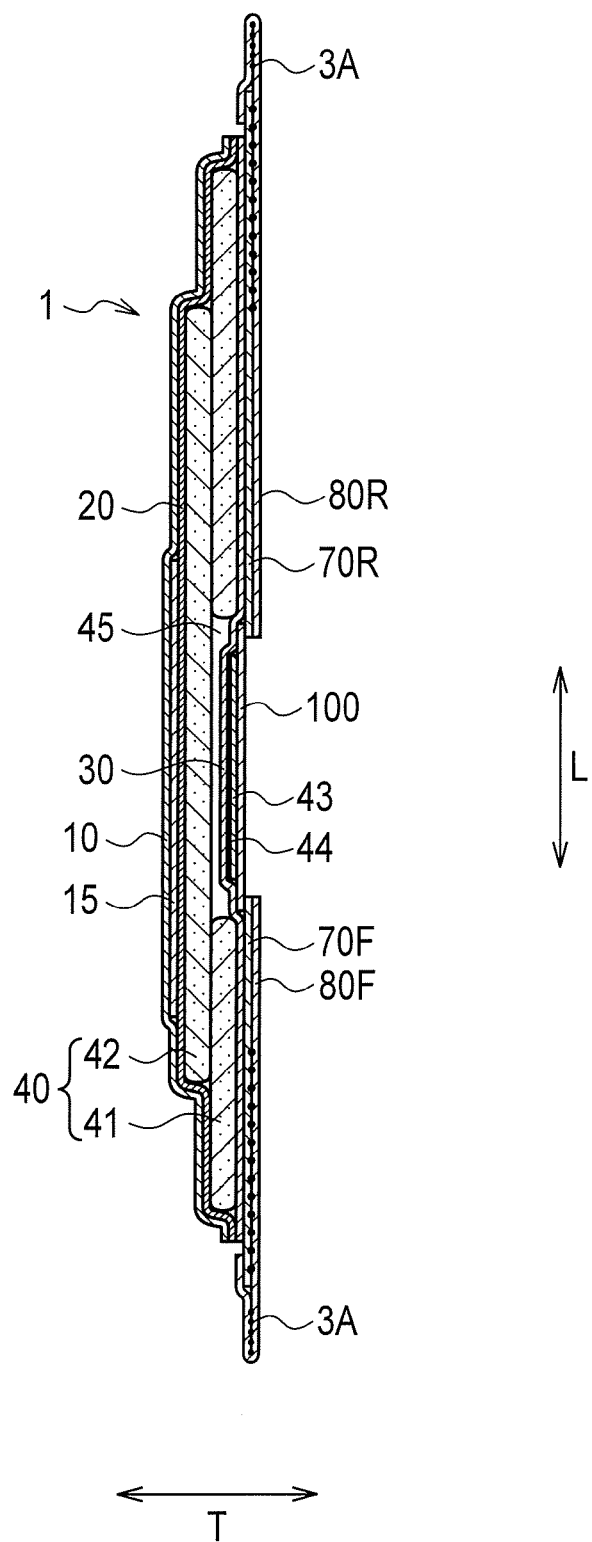
FIG. 5 is a lengthwise cross-sectional view of the disposable diaper 1 along the X2-X'2 line shown in FIG. 2.
Figure 6:
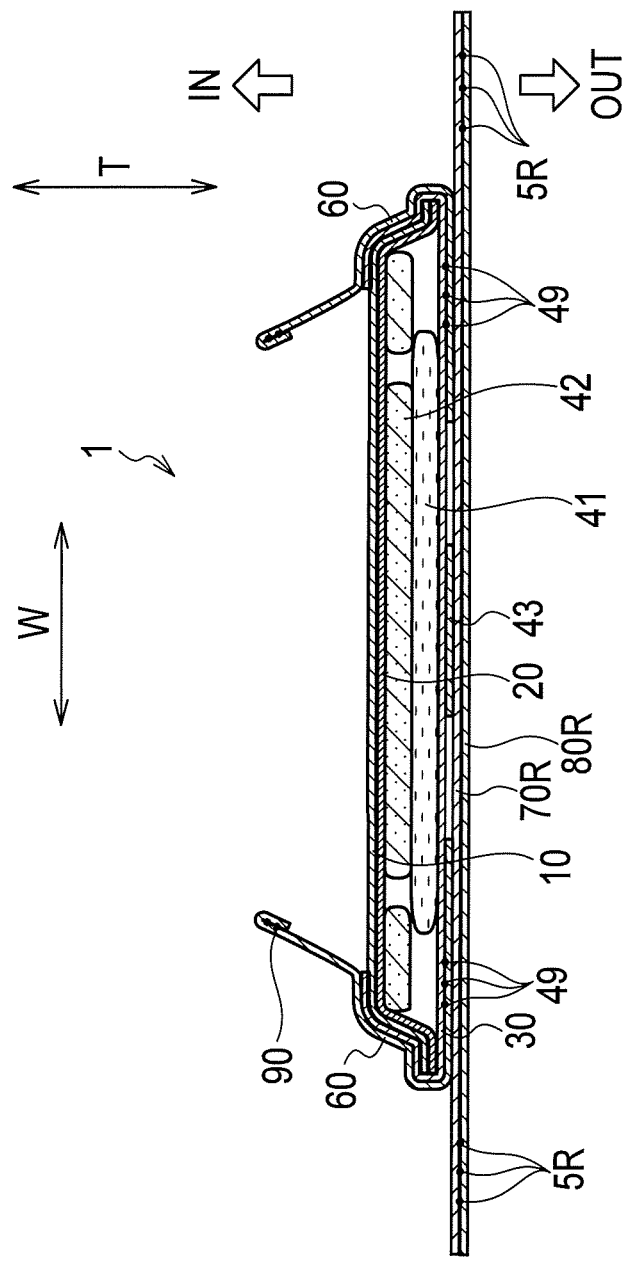
FIG. 6 is a widthwise cross-sectional view of the disposable diaper 1 along the X3-X'3 line shown in FIG. 2.

FIG. 1 is a simplified perspective schematic view of a disposable diaper 1 that configures the disposable wearing article in the present embodiment. FIG. 2 and FIG. 3 are exploded plan views of the disposable diaper 1 according to the present embodiment. FIG. 4 is a widthwise cross-sectional view of the disposable diaper 1 along the X1-X'1 line shown in FIG. 2. FIG. 5 is a lengthwise cross-sectional view of the disposable diaper 1 along the X2-X'2 line shown in FIG. 2. FIG. 6 is a lengthwise cross-sectional view of the disposable diaper 1 along the X3-X'3 line shown in FIG. 2. The disposable diaper 1 is a pant-type disposable diaper. The disposable diaper 1 includes a foreside exterior topsheet 70F, a backside exterior topsheet 70R, a foreside exterior backsheet 80F, a backside exterior backsheet 80R, and an exterior center sheet 100 configuring an exterior portion of the disposable diaper 1. An absorber 40 configured from cotton-like pulp and highly polymerized water absorbent polymer is provided on the inner side (skin contact surface side) of the foreside exterior topsheet 70F, the backside exterior topsheet 70R, and the exterior center sheet 100.

A central aperture 45 is formed in the center of the widthwise direction W in the absorber 40. Furthermore, a central elastic material 44 is provided so as to overlap the central aperture 45. A pair of side slits 42S are formed on both sides of the central aperture 45. A first elastic material 48 is provided such that at least a part overlaps the side slits 42S. As a result of the elastic materials and slits formed in the absorber 40, the absorber 40 is configured to curve when the disposable diaper 1 is worn. In the present embodiment, the central elastic material 44 configures the central curving means, and the side slits 42S and first elastic materials 48 configure the first curving means in the form of curving means.

As shown in FIG. 2, the disposable diaper 1 has a crotch region S1 that is in contact with the crotch portion of the wearer, a front region S2 arranged anterior to the crotch region S1, and a back region S3 arranged posterior to the crotch region S1 and in contact with the hip portion of the wearer. The front region S2 has a foreside middle inside leg region S21 positioned on the crotch region S1 side, and a front waistline region S22 corresponding to the front waistline and positioned anterior to the foreside middle inside leg region S21. The back region S3 has a backside middle inside leg region S31 positioned on the crotch region S1 side, and a back waistline region S32 corresponding to the back waistline and positioned posterior to the backside middle inside leg region S31.

The crotch region S1 is the region that is in contact with the crotch portion of the wearer where the width between the two legs when the wearer closes both legs is the narrowest. The foreside middle inside leg region S21 is positioned between the crotch region S1 and the front waistline region S22 in the lengthwise direction L of the absorber 40. The backside middle inside leg region S31 is positioned between the crotch region S1 and the back waistline region S32 in the lengthwise direction L.

Because a front waistline edge unit 4 joins with a back waistline edge unit 6, and at the same time, the front waistline edge unit 4' joins with the back waistline edge unit 6', the disposable diaper 1 is formed in the shape of pants.

Waist gathers 3 are provided in the front waistline region S22 and the back waistline region S32. The waist gathers 3 have an elongated waist elastic material 3A of synthetic rubber, for example, that is laid out to expand and contract along the widthwise direction W of the absorber 40. The waist elastic material 3A is joined with the foreside exterior topsheet 70F and the foreside exterior backsheet 80F, as well as the backside exterior topsheet 70R and the backside exterior backsheet 80R with an adhesive (for example, hot melt adhesive) in an extended state along the widthwise direction W of the disposable diaper 1.

Waist gathers are provided in the front region S2 and back region S3. The waist gathers have an elongated waist elastic material of synthetic rubber, for example, that is laid out to expand and contract along the widthwise direction W of the absorber 40. The waist elastic material is joined with the foreside exterior topsheet 70F and the foreside exterior backsheet 80F, as well as the backside exterior topsheet 70R and the backside exterior backsheet 80R with an adhesive (for example, hot melt adhesive) in an extended state along the widthwise direction W of the disposable diaper 1.

Leg gathers 5 are formed in the middle inside leg edge unit 8 of the backside exterior backsheet 80R. The leg gathers 5 are formed to run along the leg portions of the wearer. The leg gathers 5 are formed by a plurality of leg hole elastic materials. The leg hole elastic materials are configured from a front leg hole elastic material 5F arranged in the front region S2 and a back leg hole elastic material 5R arranged in the back region S3. A first elastic material 48 that configures a first curving means is provided between the front leg hole elastic material 5F and the back leg hole elastic material 5R in the crosswise direction.

As shown in FIG. 3, a first elongated line EL1 extending from an end 5RE on the first elastic material 48 side of the back leg hole elastic material 5R to the first elastic material 48 side along the back leg hole elastic material 5R is configured to intersect a second elongated line EL2 extending posteriorly from the back end 48B of the first elastic material 48 along the first elastic material 48. Therefore, in the region spanning the crotch region S1 and the back region S3, the leg gathers 5 are formed by the first elastic material 48 and the back leg hole elastic material 5R so as to enclose the leg hole of the wearer.

Furthermore, a third elongated line EL3 extending from an end 5FE on the first elastic material 48 side of the front leg hole elastic material 5F provided in the front region S2 to the first elastic material 48 side along the front leg hole elastic material 5F is configured to intersect the first elastic material 48. Therefore, in the region spanning the crotch region S1 and the front region S2, the leg gathers 5 are formed by the first elastic material 48 and the front leg hole elastic material 5F so as to enclose the leg hole of the wearer.

When the leg gathers 5 are formed in this way, the first elastic material 48 can be pulled up from the front by the front leg hole elastic material 5F and the first elastic material 48 can be pulled up from the back by the back leg hole elastic material 5R. Therefore, the deformation of the absorber 40 towards the inside caused by the first elastic material 48 is pulled up to the wearer side, and the stability of the convex shape of the absorber 40 towards the inside improves. Furthermore, due to the arrangement of the back leg hole elastic material 5R between the first elastic material 48 and the second elastic material 49, the effect of deformation of the absorber 40 caused by the first elastic material 48 can be prevented from reaching up to the proximity of the hip portion where the second elastic material 49 is arranged. In the proximity of the hip portion, due to the shrinkage of the second elastic materials 49 configuring the lifting units, the absorber 40 takes a stable curved shape. The deterioration in comfort when wearing the disposable diaper and the occurrence of leakage can be prevented by improving the fitting between the absorber and the wearer in the proximity of the hip portion.

Note that the first elastic materials 48 and the back leg hole elastic materials 5R, as well as the first elastic materials 48 and the front leg hole elastic materials 5F may be arranged so as to enclose the leg holes of the wearer, and another configuration can also be adopted. For example, the arrangement may be such that the first elongated line extending from the end on the first elastic material side of the back leg hole elastic material to the first elastic material side along the back leg hole elastic material intersects the first elastic material, or the back leg hole elastic material intersects the first elastic material, or else the second elongated line extending posteriorly from the back end of the first elastic material along the first elastic material intersects the back leg hole elastic material.

Additionally, the arrangement may be such that the third elongated line EL3 extending from the end on the first elastic material side of the front leg hole elastic material 5F to the first elastic material side along the front leg hole elastic material intersects the fourth elongated line EL4 extending posteriorly from the front end of the first elastic material along the first elastic material, or the first elastic material intersects the front leg hole elastic material, or else the fourth elongated line EL4 extending posteriorly from the front end of the first elastic material along the first elastic material intersects the front leg hole elastic material.

The disposable diaper 1 has a topsheet 10, an absorber 40, a sidesheet 60, a foreside exterior topsheet 70F, a backside exterior topsheet 70R, a foreside exterior backsheet 80F, and a backside exterior backsheet 80R. Each of the topsheet 10, the absorber 40, the sidesheet 60, the foreside exterior topsheet 70F and the foreside exterior backsheet 80F, the backside exterior topsheet 70R and the backside exterior backsheet 80R, the exterior center sheet 100 and the foreside exterior topsheet 70F, and the exterior center sheet 100 and the backside exterior topsheet 70R are joined with an adhesive or thermal fusion bonding.

The topsheet 10 is a sheet that forms the skin contact surface that can be in direct contact with the skin of the wearer. The topsheet 10 is formed by a liquid-permeable sheet, such as a hydrophilic nonwoven fabric and fabric, an aperture plastic film, or an aperture hydrophobic nonwoven fabric. A second sheet 15 is joined with the non-skin contact surface side of the topsheet 10.

The absorber topside covering sheet 20 is provided between the topsheet 10 and the absorber 40. The absorber topside covering sheet 20 is formed by a liquid-permeable sheet, such as a hydrophilic nonwoven fabric and fabric, an aperture plastic film, an aperture hydrophobic nonwoven fabric, or a tissue.

The absorber backside covering sheet 30 is provided on the non-skin contact surface side, which is the surface opposite the topsheet 10 and the absorber topside covering sheet 20 via the absorber 40. The absorber backside covering sheet 30 is formed by a sheet such as a liquid-impermeable film (for example, polyethylene).

The absorber 40 is covered with the absorber topside covering sheet 20 and the absorber backside covering sheet 30. The absorber 40 has a lengthwise direction L from the front waistline region S22 towards the back waistline region S32, and a widthwise direction W perpendicular to the lengthwise direction L. Additionally, the absorber 40 has an inner direction IN towards the wearer wearing the disposable diaper 1 and an outer direction OUT towards the opposite side of the inner direction.

Both the sidesheets overlap at the end of the widthwise direction of the sidesheets 60. A side elastic material 90 is provided in an extended state along the lengthwise direction L in the portion where the sidesheets overlap each other. The side elastic material 90 continues from the backside middle inside leg region S21 up to the backside middle inside leg region S31 via the crotch region S1. The side elastic material 90 is formed by synthetic rubber, etc. having elasticity.

The sidesheets 60 are provided on both ends of the widthwise direction W of the absorber 40 so as to wrap the topsheet 10, the absorber topside covering sheet 20, and the absorber backside covering sheet 30 as one part. The sidesheets 60 are formed by sheets of liquid-impermeable nonwoven fabric, and a leakage-preventing wall for preventing the side leakage of bodily waste is configured by the sidesheets 60 and the side elastic material 90.

The exterior topsheet has a foreside exterior topsheet 70F formed in the front waistline region S22 and the backside middle inside leg region S21, and a backside exterior topsheet 70R formed in the back waistline region S32 and the backside middle inside leg region S31. The exterior center sheet 100 is arranged between the foreside exterior topsheet 70F and the backside exterior topsheet 70R in the lengthwise direction. The front end of the exterior center sheet 100 is joined with the back end of the foreside exterior topsheet 70F, and the back end of the exterior center sheet 100 is joined with the front end of the backside exterior topsheet 70R. The foreside exterior topsheet 70F and the backside exterior topsheet 70R are formed such that their width in the widthwise direction W in the front waistline region S22 and the back waistline region S32 is more than any other region. The foreside exterior topsheet 70F and the backside exterior topsheet 70R can be formed by an air-through nonwoven fabric, a spun bond nonwoven fabric, an SMS nonwoven fabric, or a water-resistive film.

The foreside exterior backsheet 80F is provided towards the non-skin contact surface side from the foreside exterior topsheet 70F in the front waistline region S22. The backside exterior backsheet 80R is provided towards the non-skin contact surface side from the backside exterior topsheet 70R in the back waistline region S32. One end of the foreside exterior backsheet 80F (backside exterior backsheet 80R) in the lengthwise direction L is folded back towards the skin contact surface side, and is provided so as to wrap the ends in the lengthwise direction L of the foreside exterior topsheet 70F (backside exterior topsheet 70R). The foreside exterior backsheet 80F can be formed by an air-through nonwoven fabric, a spun bond nonwoven fabric, an SMS nonwoven fabric, or a water-resistive film.

The absorber backside covering sheet 30 is bonded partially to the foreside exterior topsheet 70F, the backside exterior topsheet 70R, and the exterior center sheet 100. As shown in FIG. 3, the absorber backside covering sheet 30 has a bonded region BA1 in which the absorber backside covering sheet 30 is bonded to at least one of the foreside exterior topsheet 70F, the backside exterior topsheet 70R, and the exterior center sheet 100, and a non-bonded region BA2 in which the absorber backside covering sheet 30 is not bonded to any of the foreside exterior topsheet 70F, the backside exterior topsheet 70R, and the exterior center sheet 100. The bonded region is the hatched region in FIG. 3. The non-bonded region BA2 is provided in the portion corresponding to the pair of first curving means. Because the exterior center sheet 100 and the absorber backside covering sheet 30 are not bonded in the portion corresponding to the first curving means, the deformation in the shape of the absorber 40 due to a deformation in the exterior center sheet, for example, can be prevented. Therefore, the stability of the convex portion of the absorber 40 formed by the first elastic material 48, for example, can be improved.

Furthermore, the non-bonded region BA2 is provided outside the lengthwise direction of a second absorber 42 that is described later in the back waistline region S32 and the front waistline region S22. The waist gathers 7 are provided in the foreside exterior topsheet 70F and the foreside exterior backsheet 80F, and the backside exterior topsheet 70R and the backside exterior backsheet 80R corresponding to the non-bonded region BA2. For example, if the foreside exterior topsheet 70F and the absorber backside covering sheet 30 are bonded, wrinkles and creases are formed in the absorber 40 due to the shrinkage of the waist elastic material 7A configuring the waist gathers 7. However, by providing the non-bonded region BA2, the occurrence of wrinkles, etc. in the absorber 40 due to shrinkage of the waist elastic material 7A can be prevented.

The central elastic material 44 is provided along the lengthwise direction L, and is provided at a position where the central elastic material 44 overlaps the central aperture 45 in the thickness direction T of the disposable diaper 1. The central elastic material 44 is formed in a convex shape in the inner direction IN, that is, the central elastic material 44 is formed so as to overlap the absorber 40 along the lengthwise direction L such that the absorber 40 curves in a convex shape towards the wearer.

The first elastic material 48 is provided in the lengthwise direction L at a position where the first elastic material 48 overlaps the side slits 42S, which are described later, in the thickness direction T of the disposable diaper 1. The first elastic material 48 is formed in a convex shape in the inner direction IN, that is, the first elastic material 48 is formed so as to overlap the absorber 40 along the lengthwise direction L such that the absorber 40 curves in a convex shape towards the wearer.

The central elastic material 44 and the first elastic material 48 are provided in an extended state on the non-skin contact surface side of the absorber backside covering sheet 30. Furthermore, an elastic material covering sheet 43 is provided in the non-skin contact surface side of the central elastic material 44, and the central elastic material 44 is joined between the absorber backside covering sheet 30 and the elastic material covering sheet 43 with an adhesive. Additionally, the sidesheets 60 are provided in the non-skin contact surface side of the first elastic material 48, and the first elastic material 48 is joined between the absorber backside covering sheet 30 and the sidesheets 60 with an adhesive. Note that the central elastic material 44 and the first elastic material 48 may be joined either with the topsheet 10 or with the foreside exterior topsheet 70F and the backside exterior topsheet 70R.

Furthermore, the front end 44F of the central elastic material 44 is arranged posterior to the front end 48F of the first elastic material 48. That is, the front end of the central curving mean is provided posterior to the front end of the first curving means. According to such a configuration, a gap is easily formed anterior to the wearer in the crotch portion, and deterioration in comfort when wearing the disposable diaper due to compression of the front of the crotch portion can be prevented.

On the other hand, the back end 48B of the first elastic material 48 is arranged anterior to the back end 44B of the central elastic material 44. That is, the back end of the first curving means is provided anterior to the back end of the central curving means. When the first curving means becomes too long in the posterior direction, the first curving means extends up to the proximity of the hip portion, and the absorber 40 cannot easily follow along the curve of the hip portion. However, according to such a configuration, the worn article can easily take the shape of a smooth curve, the worn article can be arranged along the hip portion, and an appropriate gap can be maintained between the worn article and the skin. Therefore, bodily waste such as the excreted urine and stool can be accumulated temporarily in the gap between the worn article and the skin, and leakage of bodily waste such as fluid leakage can be prevented. Furthermore, the worn article takes a shape along the hip portion, and therefore, the outer shape of the worn article is the shape along the body, and a good appearance can be maintained.

Examples of the material of the central elastic material 44 include synthetic rubber such as styrene-butadiene, butadiene, isoprene, and neoprene, natural rubber, EVA, elastic polyolefin, spandex, and foamed polyurethane. Besides this, an elastic sheet such as an elastic nonwoven fabric can be used as the material of the central elastic material 44.

In the first embodiment, the central elastic material 44 has three central elastic members 44C arranged in parallel across approximately 10 mm, and central auxiliary elastic members 44S arranged in parallel in twos sideways of the central elastic members 44C in the widthwise direction W. The length of the central elastic material 44 in the lengthwise direction L is approximately 120 mm. Three central elastic members 44C are extended and fixed at a thickness of 620 dtex and an extension magnitude of 2.5 times, and central auxiliary elastic members 44S are extended and fixed in twos outside the widthwise direction of the central elastic materials at a thickness of 620 dtex and an extension magnitude of 1.8 times. The material of the central elastic materials 44 is spandex. In the state prior to when the absorber curves in a convex shape, in the central elastic material 44, the central elastic members 44C positioned in the center of the central elastic material in the widthwise direction are provided such that the extension stress is more than the extension stress of the central auxiliary elastic members 44S provided outside the widthwise direction of the central elastic members 44C. Therefore, as a result of the central elastic material 44, a convex shape is formed more precisely in the inner direction IN, that is, the absorber 40 can curve towards the wearer in a convex shape. Furthermore, the curve of the hill of the convex shape becomes gentle sloped, and the area in close contact with the skin can be increased. The extension magnitude of the central elastic members 44C is desired to be in the range of 1.4 times to 3.0 times, and the extension magnitude of the central auxiliary elastic members 44S is desired to be in the range of 1.2 times to 2.8 times.

Three first elastic materials 48 are arranged in parallel in the widthwise direction W. The material of the first elastic material 48 is spandex. The first elastic material 48 is extended and fixed in threes at a thickness of 620 dtex and an extension magnitude of 2.0 times. Note that the first elastic material 48 is configured so as to have an extension stress lesser than that of the central elastic material 44 in the state prior to when the absorber 40 is curved in a convex shape. In other words, the state prior to when the absorber curves in a convex shape is the state in which the worn article is extended in a plane, as shown in FIG. 2. By configuring the first elastic material 48 such that the extension stress is lesser than that of the central elastic material 44, the height of the convex portion formed by the central elastic material 44 becomes more than that of the convex portion formed by the first elastic material 48. Therefore, the convex portion of the central region can be brought into close contact with the excretion portion side of the wearer at the time of wearing.

Furthermore, the second elastic materials 49 configuring the lifting units, which exist posterior to the central elastic material 44 and the first elastic material 48, are provided outside the widthwise direction of the central elastic material 44 and the first elastic material 48. The second elastic material 49 is provided at a position where the second elastic material 49 overlaps the absorber 40 in the thickness direction T of the disposable diaper 1. The second elastic material 49 is configured such that by lifting up the absorber 40 in the inner direction, the worn article in the proximity of the hip portion can be shrunk towards the inner direction IN and the worn article can take a shape along the hip portion.

The material of the second elastic material 49 is spandex, and three second elastic materials 49 are arranged in parallel in the widthwise direction W. The second elastic material 49 is extended and fixed at a thickness of 780 dtex and an extension magnitude of 2.3 times. For example, as shown in FIG. 14 (*e*), which is described later, when the first elastic material 48 and the second elastic material 49 overlap in the widthwise direction W (when the first elastic material 48 and the second elastic material 49 are arranged adjacent to each other in the widthwise direction), the extension stress of the first elastic material 48 is configured to become more than the extension stress of the second elastic material 49 in the overlapping portion in the state prior to when the absorber 40 curves in a convex shape and in the state prior to when the absorber 40 is lifted up in the inner direction. By configuring the second elastic material 49 such that the extension stress of the second elastic material 49 is lesser than that of the first elastic material 48, the portion in which the first elastic material 48 is arranged is deformed so as to come closer to the body at the time of wearing. Therefore, the absorber 40 that is positioned outside the widthwise direction from the first elastic material 48 curves stably towards the outside. By stably curving the portion of the absorber 40 that is in contact with the crotch portion of the wearer towards the outside, for example, even when the width of the absorber is increased in order to enhance the absorbing power of the crotch portion, the absorber 40 and the excretion portion can be easily brought into close contact. Note that the extension magnitude of the first elastic materials 48 is desired to be in the range of 1.2 times to 3.2 times, and the extension magnitude of the second elastic materials is desired to be in the range of 1.5 times to 3.5 times.

The first elastic materials 48 and the second elastic materials 49 are provided such that they do not overlap in the widthwise direction W. That is, the first elastic materials 48 and the second elastic materials 49 are alienated in the lengthwise direction L, and the back ends 48B of the first elastic materials 48 are positioned anterior to the front ends 49F of the second elastic materials 49. The first elastic materials 48 curve the absorber 40 such that the absorber 40 takes a convex shape towards the inner direction IN. A valley is provided for the hill, which is the convex shape in the inner direction IN, outside the widthwise direction from the first elastic materials 48. The second elastic material 49 is arranged outside the widthwise direction from the first elastic material 48, and biases the absorber 40 towards the inner direction IN. If the first elastic materials 48 and the second elastic materials 49 are arranged close to each other, the valley corresponding to the hill of the first elastic materials 48 is pushed up due to the biasing force of the second elastic materials 49, and the stability of the convex portion formed by the first elastic materials might decline. Therefore, the first elastic materials 48 and the second elastic materials 49 are desired to be provided such that they do not overlap in the widthwise direction W. Furthermore, when the first elastic materials 48 and the second elastic materials 49 overlap in the widthwise direction W, the length of the lengthwise direction L of the overlapping region is desired to be 20 mm or less.

Note that in the present embodiment, the first elastic materials 48 and the second elastic materials 49 are arranged such that they do not overlap in the widthwise direction, however, the first elastic materials 48 and the second elastic materials 49 may be arranged such that they overlap in the widthwise direction W. In such a case, at least the back ends 48B of the first elastic materials 48 are desired to be arranged anterior to the back ends 49B of the second elastic materials 49.

It is desired that the first elastic materials 48 not be arranged posterior to the crotch region S1 (in the back region S3). By not arranging the first elastic materials 48 in the back region S3, the absorber 40 between the pair of first elastic materials in the back region S3 is turned stably towards the inside. The worn article can easily take the shape of a smooth curve, the worn article can be arranged along the hip portion, and an appropriate gap can be maintained between the worn article and the skin. By providing the gap, in cases where the absorption speed of the absorber does not match up to the excreted urine, the urine can be accumulated temporarily, and leakage can thus be prevented. Furthermore, because the gap between the skin and the absorber also functions as a space for accommodating stools, the leakage of stools can also be prevented.

Additionally, in the proximity of the hip portion where there are maximum chances of leakage when the wearer is lying down, because the absorber is lifted up towards the wearer by the lifting units so as to come in close contact with the skin, the urine that is transferred on to the skin can be prevented from flowing out. Furthermore, the worn article takes a shape along the hip portion, and therefore, the outer shape of the worn article is the shape along the body, and a good appearance can be maintained.

Figure 7:
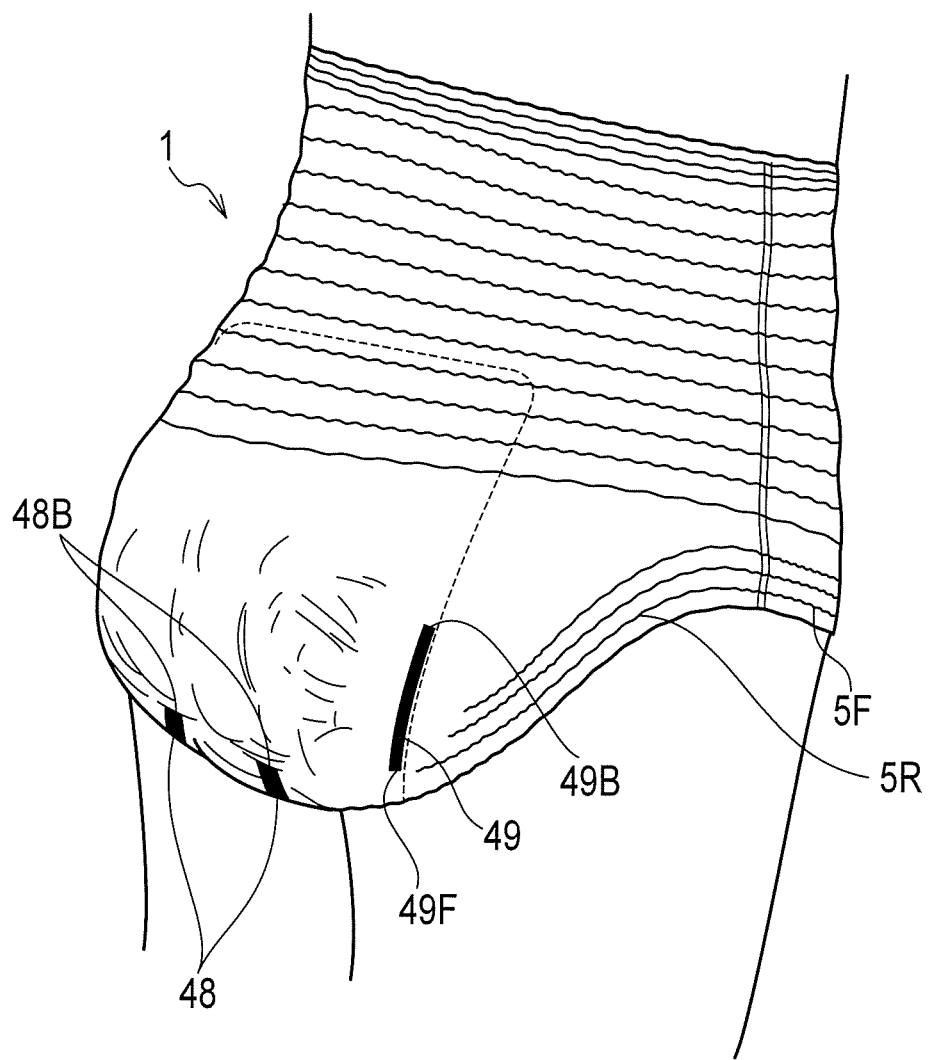
FIG. 7 is a simplified perspective view that schematically illustrates the wearing state of the disposable diaper 1 according to the first embodiment.
Figure 8:
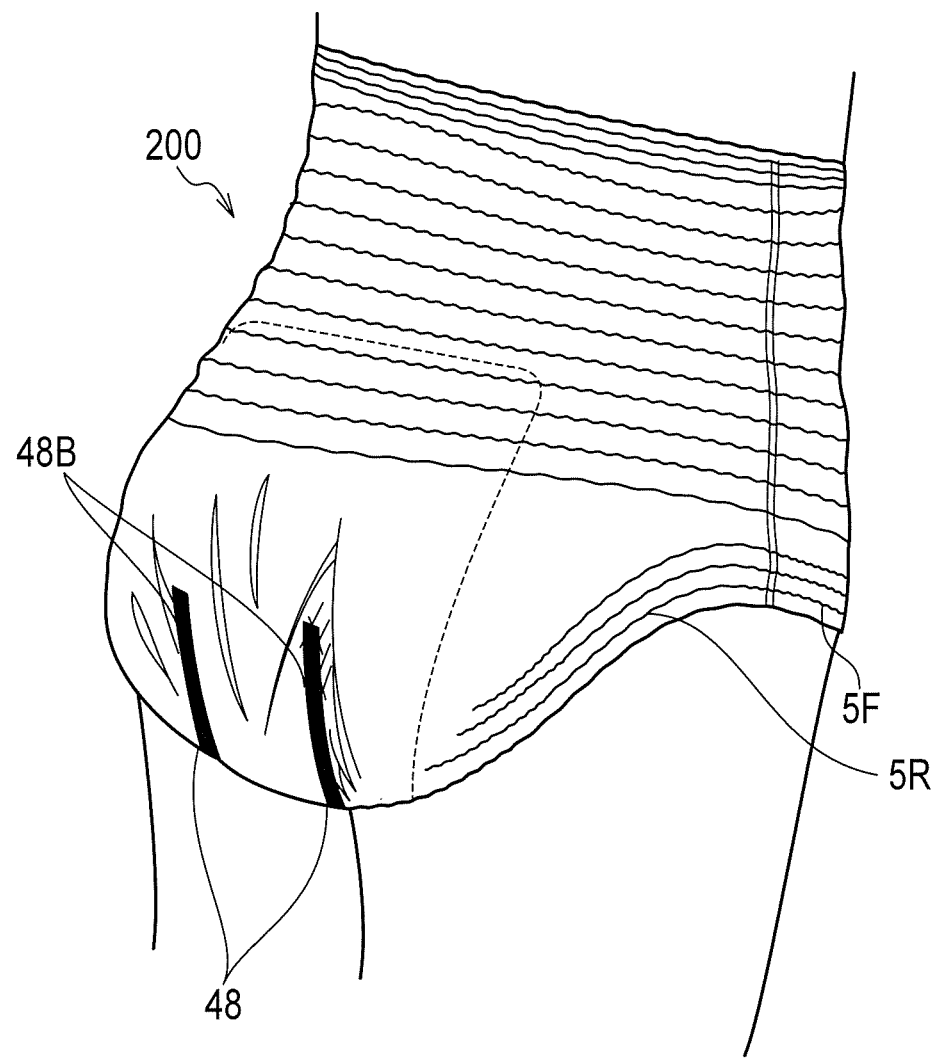
FIG. 8 is a simplified perspective view that schematically illustrates the wearing state of the disposable diaper 200 according to a comparative example.

FIG. 7 is a simplified perspective view that schematically illustrates the wearing state of the disposable diaper 1 according to the first embodiment, and FIG. 8 is a simplified perspective view that schematically illustrates the wearing state of the disposable diaper according to a comparative example. The disposable diaper according to the comparative example is different from the disposable diaper according to the present embodiment, and does not have the second elastic materials 49. Additionally, the length of the disposable diaper according to the comparative example in the lengthwise direction L of the first elastic materials 48 is configured to be 30 mm longer towards the back side as compared to the disposable diaper according to the present embodiment. Therefore, the first elastic materials 48 of the disposable diaper according to the comparative example extend up to the hip portion.

As shown in FIG. 8, when the back ends 48B of the first elastic materials 48 extend up to the hip portion, the convex portion resulting due to the first elastic materials 48 extends posteriorly, and a folding line extending in the lengthwise direction L is formed in the back region S3. Therefore, it becomes difficult for the absorber 40 to be arranged in a curved shape. On the other hand, as shown in FIG. 7, when the first elastic materials 48 and the second elastic materials 49 do not overlap in the widthwise direction, the absorber stably takes a curved form in the proximity of the hip portion, and the outer shape of the worn article becomes the shape along the body, and a good appearance can be maintained while keeping an appropriate gap between the absorber and the wearer.

Note that the extension stress of the elastic materials can be measured as described below, for example.

[1] Cut out the whole material holding in between an elastic material such that all elastic materials forming the convex portion are included in the widthwise direction. Specifically, in the worn article according to the present embodiment, the material holding in between the three central elastic materials arranged at an interval of 5 mm and the first elastic material is cut out at a width of 13 mm and a length of 100 mm in an extended state such that there is no sagging. Again in the extended state, markings are made on the inside at 10 mm from both ends in the lengthwise direction. A tensile tester made by Instron Japan Co., Ltd. (for example, model no. 5564), or Autograph by Shimadzu Corporation (for example, model no. AGS-1kNG) is used for measuring the extension stress.

[2] Hold the test sample of [1] between the upper chuck and the lower chuck such that the marking coincides with the inner end of the upper chuck, and the marking on the other side coincides with the inner end of the lower chuck. The length of the test sample between the chucks is 80 mm. Note that when the effective length of the gathers of the elastic materials is shorter than 100 mm, the length that is 20 mm shorter than the shortest length in the effective length of the gathers of the elastic materials is set as the length of the test sample between the chucks. The initial distance between the chucks is set shorter than the length (natural length) when the test sample is compressed in between such that the tension of the test sample is not exerted initially. In order to alienate the chucks from each other, the test sample is pulled up and down under a condition of 100 mm/min., and the test sample is extended.

[3] By assuming the length of the test sample between the chucks at the time of extension of the material holding the elastic members without any sagging as 100%, the test sample is extended such that the length of the test sample between the chucks becomes 90%, and the stress during extension of the test sample is measured and set as the extension stress of the elastic material. That is, in the above embodiment, the extension stress when the test sample is extended up to 72 mm, which is 90% of 80 mm—the 100% length of the text sample, is measured.

Furthermore, the absorber topside covering sheet 20 may be configured to be joined with the absorber backside covering sheet 30 in the portion in which the side slits 42S are formed. By thus configuring, closing of the side slits 42S due to deformation of the absorber 40, and misalignment of the absorber topside covering sheet 20 and the absorber 40 can be prevented. Furthermore, when the absorber 40 swells up by absorbing the fluid, a convex portion can be formed perfectly by the side slits 42S in order to prevent the side slits 42S from closing.

As for each member configuring the aforementioned disposable diaper 1, the material described in Japanese Unexamined Patent Application Publication No. 2006-346439 may be used.

(2) Structure of the Absorber

Figure 9:
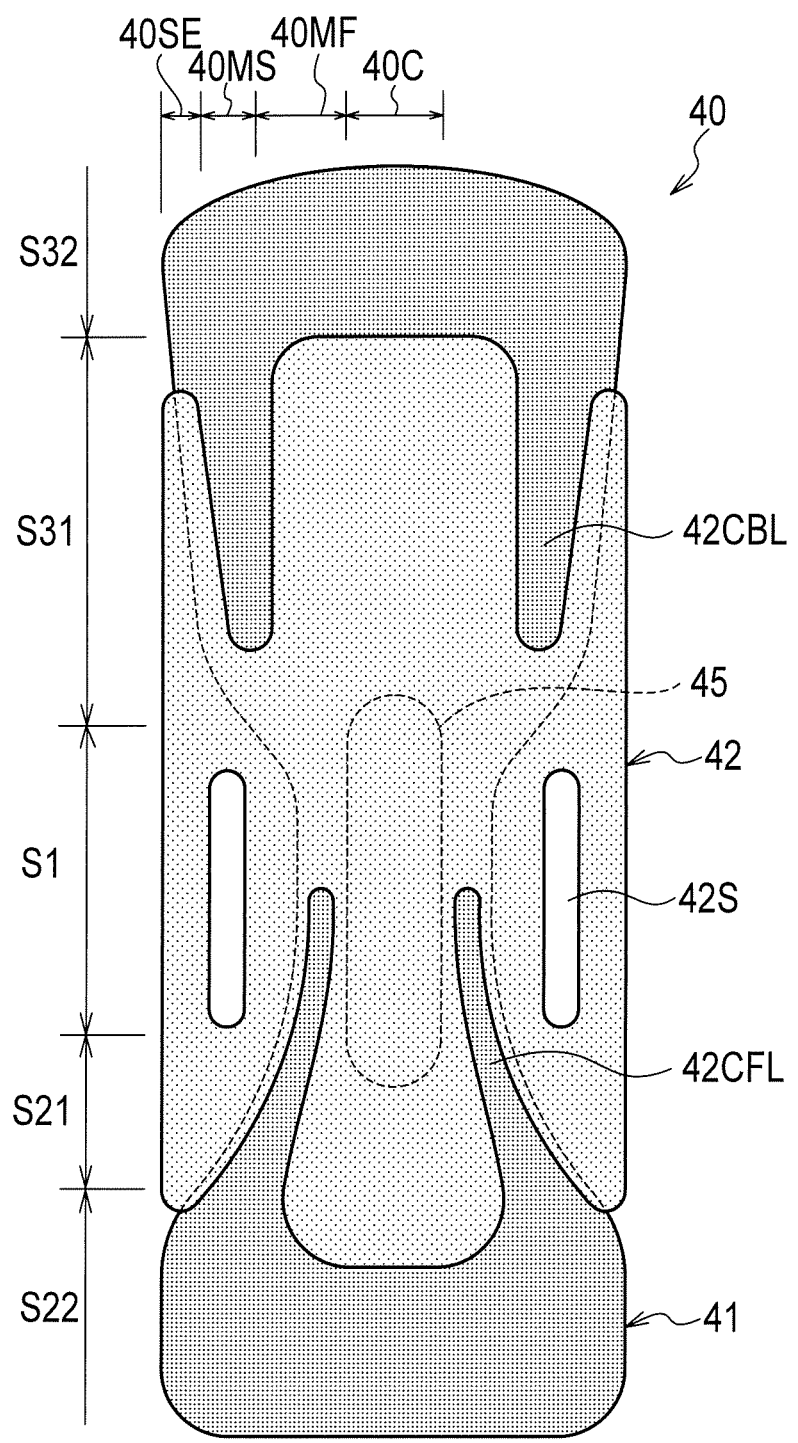
FIG. 9 is a plan view of an absorber according to the first embodiment.
Figure 10:
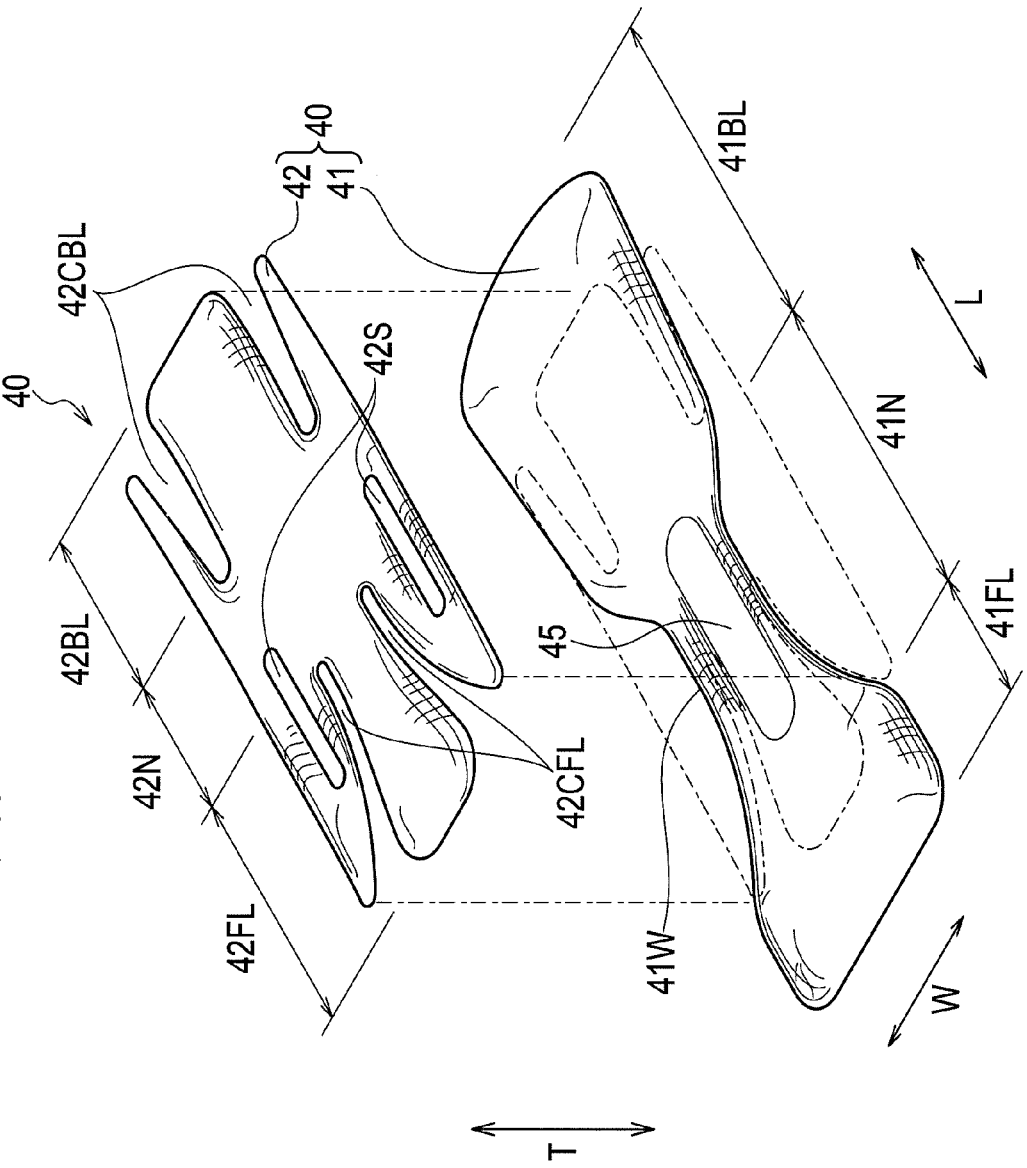
FIG. 10 is a perspective view of the absorber according to the first embodiment.

FIG. 9 is a plan view of the absorber 40 and FIG. 10 is a perspective view of the absorber 40. As shown in FIG. 9 and FIG. 10, the absorber 40 has a first layer 41 and a second layer 42 overlapping the first layer 41. The first layer 41 is positioned at the non-skin contact surface side of the wearer, and the second layer 42 is positioned at the skin contact surface side of the wearer.

The first layer 41 and the second layer 42 are configured by cotton-like pulp and highly polymerized absorbent polymer (SAP). The first layer 41 is formed by mixing together 270 g/m$^2$ of pulp and 170 g/m$^2$ of SAP, and its thickness in the thickness direction T is approximately 3.0 mm. The second layer 42 is formed by mixing together 400 g/m$^2$ of pulp and 240 g/m$^2$ of SAP, and its thickness in the thickness direction T is approximately 4.4 mm. That is, the thickness of the portion in which the first layer 41 and the second layer 42 overlap is approximately 7.4 mm. Note that the first layer 41 is desired to have 100 to 500 g/m$^2$ of pulp and 20 to 500 g/m$^2$ of SAP, and the second layer 42 is desired to have 100 to 500 g/m$^2$ of pulp and 0 to 500 g/m$^2$ of SAP.

As shown in FIG. 10, the first layer 41 recesses towards the center of the widthwise direction W, and has a narrow unit 41N having a predetermined width in the widthwise direction W, and wide units 41FL and 41BL formed on both ends of the narrow unit 41N in the lengthwise direction L. The narrow unit 41N is formed in the crotch region S1. Furthermore, the wide unit 41FL is formed in the front waistline region S22, and the wide unit 41BL is formed in the back waistline region S32. The side ends of the narrow unit 41N and the side ends of the wide units 41FL and 41BL are connected by a curved line, and the first layer 41 has a planar shape in the form of an hourglass.

Furthermore, the central aperture 45 is formed in the center of the widthwise direction W in the first layer 41. The central aperture 45 has a longitudinally elongated shape extending along the lengthwise direction L, and is formed across the crotch region S1, the backside middle inside leg region S21, and the backside middle inside leg region S31. The length of the central aperture 45 is approximately 180 mm, and the width is approximately 40 mm. By thus forming the central aperture 45, the central portion 40C can be easily curved in a convex shape in the inner direction IN, which is the wearer's side. Furthermore, by improving the diffusive property of the bodily fluid in the crosswise direction of the absorber, and by diffusing the bodily fluid in a wide range, the absorption performance can be improved.

Furthermore, the density of the narrow unit 41N of the first layer 41 is configured to be more than the density of the wide unit 41FL of the first layer 41, which is more than the density of the wide unit 41BL of the first layer 41. Additionally, the density of the narrow unit 41N of the first layer 41 is more than the density of the second layer 42. Therefore, the rigidity of the narrow unit 41N of the first layer 41 becomes more than that of the other portions of the first layer 41 and the second layer 42.

The second layer 42 has a notched unit 42FL in which a notch is formed from the front end towards the center, a notched unit 42BL in which a notch is formed from the back end towards the center, and a central unit 42N positioned between the notched unit 42FL and the notched unit 42BL.

The length of the widthwise direction of the second layer 42 is more than that of the narrow unit 41N of the first layer 41, and is almost same as the length of the widest portion in the wide units 41BL and 41FL of the first layer 41. A notch 42CFL and a notch 42CBL are formed extending towards the center from both ends in the crosswise direction in the second layer.

A pair of side slits 42S are formed in the second layer 42. The side slits 42S are formed in a convex shape in the inner direction IN, that is, the side slits 42S are formed in the absorber 40 along the lengthwise direction L such that the absorber 40 curves in the same convex shape as the central aperture 45. The length of the side slits 42S is shorter than that of the central aperture 45 and the width of the side slits 42S is narrower than that of the central aperture 45. Specifically, the length of the side slits 42S is approximately 110 mm, and the width is approximately 15 mm.

The notch 42CFL is formed across the backside middle inside leg region S21 and the front waistline region S22, and the notch 42CBL is formed in the backside middle inside leg region S31. The aperture shape of the notch 42CFL extends in the widthwise direction inner side towards the center.

Both outer edges in the widthwise direction of the notch 42CFL have almost the same width as both outer edges in the widthwise direction of the narrow unit 41N of the first layer 41 in the crotch region S1 and the backside middle inside leg region S21. According to such a configuration, the width of the anterior portion of the absorber when the legs are closed and folded while wearing the worn article can be reduced. Therefore, the thickness of the absorber in the front of the body of the wearer is reduced, and the uncomfortable feeling in the crotch portion can be lessened.

Both outer edges in the widthwise direction of the notch 42CBL have almost the same width as both outer edges in the widthwise direction of the wide unit 41BL of the first layer 41 in the backside middle inside leg region S31. According to such a configuration, when the absorber swells up due to absorption of the bodily fluid, a gap can be maintained easily between the absorber and the skin of the wearer. Additionally, by providing the notch 42CBL, the bodily fluid can be transferred smoothly from the second layer 42 to the first layer 41, and the performance of the absorber can be put to use effectively.

In the crotch region S1, the outer ends 41W in the widthwise direction of the first layer 41 are arranged along the crosswise direction. The outer sides of the widthwise direction from the outer ends 41W of the absorber 40 are configured only by the second layer 42, and the inner sides from the outer ends 41W are configured by the first layer 41 and the second layer 42, excluding the portion in which the central aperture 45 is formed. Therefore, the rigidity and thickness of the absorber 40 change with the outer ends 41W of the first layer 41 as the boundary. According to the present embodiment, the absorber curves with the outer ends 41W of the first layer, where the rigidity, etc. change, as the boundary. That is, the outer ends 41W of the first layer 41 configure the second curving means where the absorber 40 curves in the outer direction in a convex shape. Thus, according to the configuration in which the convex portion is formed with the outer ends 41W of the first layer, where the thickness, etc. of the absorber 40 change, as the boundary, as compared to a configuration in which the convex portion is formed by slits, the convex portion can be formed while maintaining the absorption performance because there is no need to form an aperture by the slits in the proximity of the convex portion. Note that the outer ends 41W in the widthwise direction of the first layer 41 are edge sides along the crosswise direction of the first layer. Therefore, the second curving means is formed along the crosswise direction.

The absorber 40 thus configured by the first layer 41 and the second layer 42 has a central portion 40C, a first intermediate portion 40MF, a second intermediate portion 40MS, and side end portions 40SE, as shown in FIG. 4. The central portion 40C is formed in the center of the absorber 40 in the widthwise direction W. The intermediate portion is positioned between the central portion 40C and the side end portions 40SE. The intermediate portion has the first intermediate portion 40MF and the second intermediate portion 40MS. The first intermediate portion 40MF is positioned between the central portion 40C and the second intermediate portion 40MS. A convex portion is formed in the first intermediate portion 40MF by the second curving means. The second intermediate portion 40MS is positioned between the first intermediate portion 40MF and the side end portions 40SE. A convex portion is formed in the second intermediate portion 40MS by the first curving means. The side end portions 40SE are formed in the side ends of the absorber 40 in the widthwise direction W.

According to the present embodiment, in the crotch region S1, the central portion 40C, the second intermediate portion 40MS, and the side end portions 40SE are formed only by the second layer 42. On the other hand, the first intermediate portion 40MF has a portion formed only by the second layer 42, and a portion formed by the first layer 41 and the second layer 42. Therefore, the thickness of the absorber 40 in a part of the first intermediate portion 40MF is more than the thickness of the absorber 40 in the central portion 40C and the side end portions 40SE.

The thickness of the absorber 40 is measured by inserting the portion to be measured in the thickness measurement gauge when the absorber 40 has been extended to the product length and the product width (that is, a planar state in which no wrinkles are formed). A thickness gauge manufactured by PEACOCK (measurement part: 5-mm diameter, pressure at the time of measurement: 163 g/cm$^2$) can be used as the measurement device, for example.

According to the present embodiment, the first layer 41 and the second layer 42 are formed as one by being pressed along the thickness direction T. Note that the first layer 41 and the second layer 42 can also be formed as one with an adhesive and thermal fusion bonding. Furthermore, in the absorber 40, the first layer 41 is positioned in the non-skin contact surface side and the second layer 42 is positioned in the skin contact surface side, but the second layer 42 can be positioned in the non-skin contact surface side and the first layer 41 can be positioned in the skin contact surface side.

(3) Changes in the Shape of the Absorber

Figure 11:
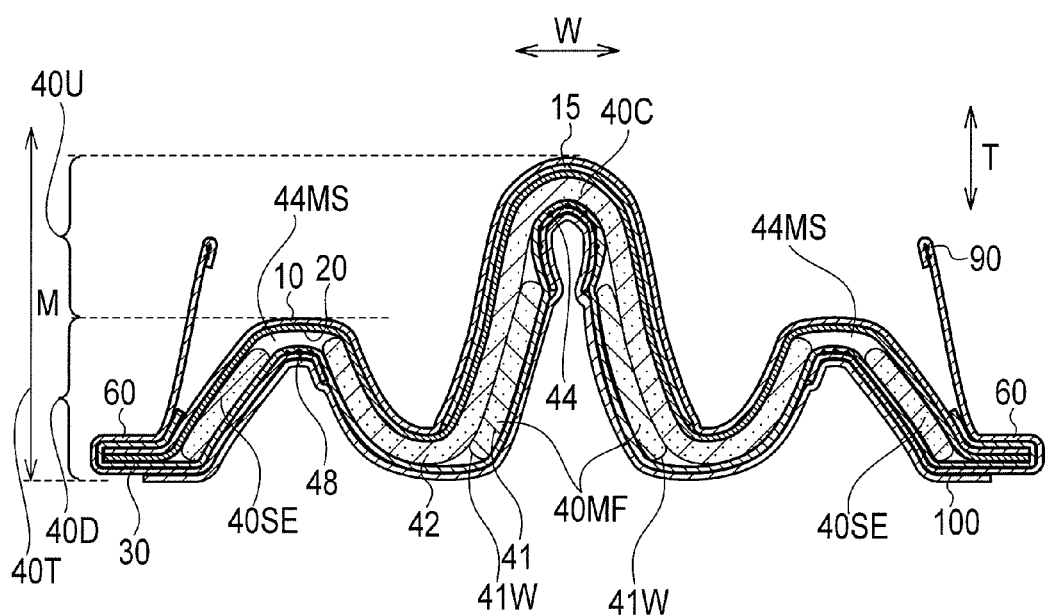
FIG. 11 is a cross-sectional view along the X1-X'1 line that schematically illustrates the wearing state of the disposable diaper 1 according to the first embodiment.

FIG. 11 is a cross-sectional view (with reference to the X1-X'1 line of FIG. 2) that schematically illustrates the wearing state of the disposable diaper 1. As shown in FIG. 11, when the disposable diaper 1 is worn, the absorber 40 curves with the central elastic material 44, the first elastic material 48, and the outer ends 41W in the widthwise direction of first layer 41 as the base points, and the cross-section shape of the disposable diaper 1 along the widthwise direction W changes to a wavy form. As a result, the top surface of the absorber 40 that takes a convex shape in the inner direction IN as a result of the central elastic material 44 comes in contact with the crotch portion of the wearer. Furthermore, the central portion 40C is positioned in the upper region 40U closer to the body of the wearer from the virtual line M dividing the height 40T of the deformed absorber 40 into two. On the other hand, the first intermediate portion 40MF, the second intermediate portion 40MS, and the side end portions 40SE are positioned in the lower region 40D away from the body of the wearer from the virtual line M.

The central portion 40C in which a convex portion is formed by the central curving means is configured only by the second layer 42, and its thickness is relatively low. In the first intermediate portion 40MF between the convex portion formed by the central curving means and the convex portion formed by the second curving means, the first layer and the second layer are overlapping, and the thickness is relatively high. Additionally, the density of the crotch region S1 of the first layer 41 is comparatively higher than the density of the other regions in the first layer 41, and the rigidity is high. The convex portion formed by the central curving means can be supported by the portion between the central curving means and the second curving means having a high rigidity, and the stability of the convex shape formed by the central curving means can be improved.

Note that the side edges 50A (leg standing gathers) including the side elastic material 90 are desired to be positioned at a higher position than the central portion 40C, that is, towards the wearer in the thickness direction T of the figure.

Figure 12:
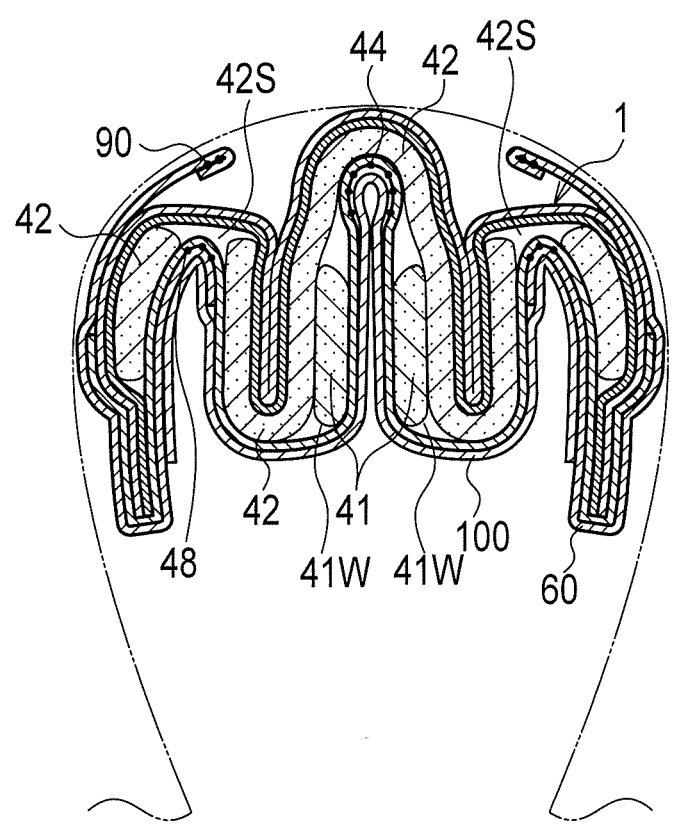
FIG. 12 is a cross-sectional view (when the legs are closed) that schematically illustrates the wearing state of the disposable diaper 1 according to the first embodiment.

FIG. 12 is a cross-sectional view (with reference to the X1-X'1 line of FIG. 2) that schematically illustrates the wearing state of the disposable diaper 1 when the wearer has closed the legs. Note that the virtual line in the figure shows the crotch portion and both leg portions of the wearer.

As shown in FIG. 12, when the wearer closes both legs, the cross-sectional shape of the disposable diaper 1 changes from the state shown in FIG. 11 to the state shown in FIG. 12. When the wearer closes both legs, the central portion 40C and the second intermediate portion 40MS are positioned to be in contact with the crotch portion of the wearer. On the other hand, the first intermediate portion 40MF and the side end portions 40SE are positioned downward (inner leg side) from the central portion 40C.

Figure 13:
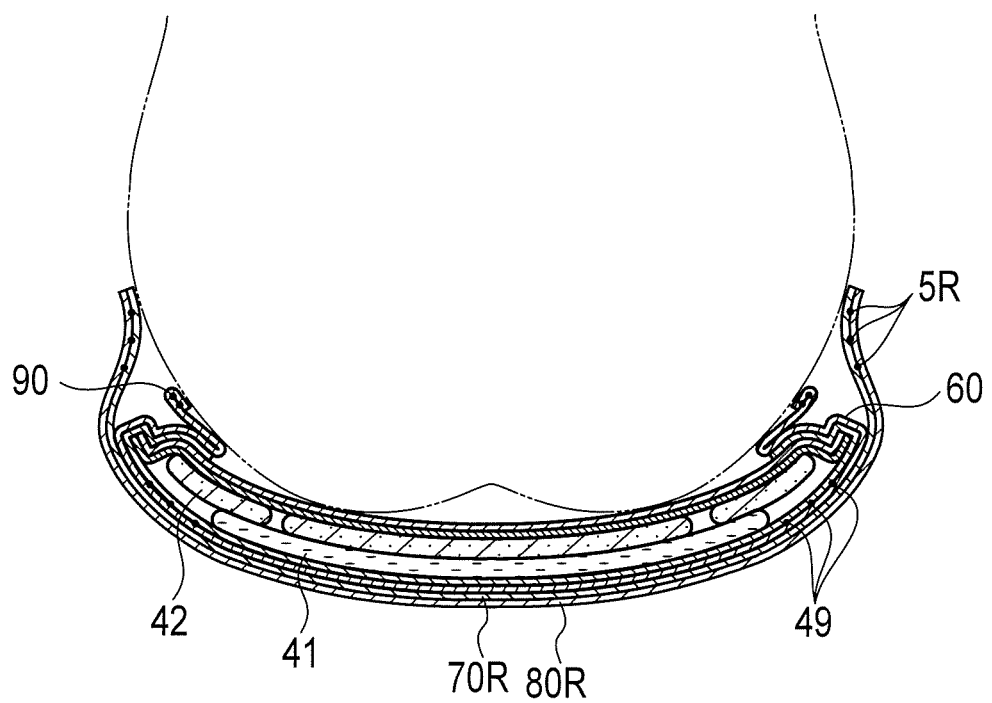
FIG. 13 is a cross-sectional view along the X3-X'3 line that schematically illustrates the wearing state of the disposable diaper 1 according to the first embodiment.

Furthermore, FIG. 13 is a cross-sectional view (with reference to the X3-X'3 line of FIG. 2) that schematically illustrates the wearing state of the disposable diaper 1. As shown in FIG. 13, when the disposable diaper 1 is worn, the portion corresponding to the second elastic materials 49 of the absorber 40 is lifted up towards the body of the wearer due to the second elastic materials 49. The first elastic materials 48 are not provided between the second elastic materials 49 in the widthwise direction W. Therefore, the absorber 40 does not get deformed into a convex shape due to the first elastic materials 48, but takes a curved shape along the hip portion.

Furthermore, the aforementioned disposable diaper 1 has a central elastic material 44 and a first elastic material 48 formed in the absorber 40 to enable the absorber 40 to curve in a convex shape in the inner direction IN, and a pair of side slits 42S formed in the absorber 40 to enable the absorber 40 to curve in a convex shape in the outer direction OUT. The distance between the central elastic material 44 configuring the central curving means and the outer ends 41W of the first layer 41 configuring the second curving means in the widthwise direction is longer than the distance between the outer ends 41W and the first elastic material configuring the second curving means in the widthwise direction. Therefore, the height of the convex portion of the central portion 40C is more than the height of the convex portion of the second intermediate portion 40MS. As a result, when the disposable diaper 1 is worn, the central portion 40C that takes a convex shape towards the excretion portion of the wearer easily comes in close contact with the excretion portion. Furthermore, because the first intermediate portion 40MF forms a recessed unit, the bodily waste can easily enter the recessed unit, and the skin of the wearer can be prevented from coming in direct contact with the bodily waste.

Particularly, because the central aperture 45 is formed in the portion of the central elastic material 44, and the side slits 42S are formed in the absorber 40, the absorber 40 can be curved easily not only in cases where the absorber 40 is formed into a convex portion by forming a thin portion in the absorber 40, but also when the absorber 40 swells up by absorbing the fluid. Furthermore, the cross-sectional shape when the absorber 40 is deformed at the time of wearing the disposable diaper 1 becomes tapered as the absorber takes a narrow form from the inner leg towards the crotch portion, and because the absorber easily enters the gap in the crotch portion of the wearer, the wearer does not experience discomfort.

Furthermore, the convex portion formed by the central curving means is configured only from the second layer, and is thinner than the portion configured by the lamination of the first layer 41 and the second layer 42. In other words, due to a thin and high structure, the convex portion formed by the central curving means can be easily inserted in the thin gap of the crotch portion, and easily comes in close contact with the excretion portion. Therefore, because the excretion portion and the absorber come in close contact, for example, the excreted urine can be absorbed rapidly.

Additionally, in the crotch region S1, the density of the absorber 40 positioned between the second curving means and the central curving means is configured to be more than the density of the absorber 40 of the central portion 40C and the side end portions 40SE. That is, the rigidity of the absorber 40 positioned between the second curving means and the central curving means is configured to be more than that of the absorber 40 of the central portion 40C and the side end portions 40SE, and more than that of the absorber 40 outside the widthwise direction from the second curving means. The absorber 40 positioned between the second curving means and the central curving means is positioned outside the widthwise direction of the central curving means, and supports the central convex portion. Because the density of the absorber 40 positioned between the second curving means and the central curving means is high, even when the central curving means comes in contact with the excretion portion and is pressed by the body of the wearer, the central curving means can be maintained in an upright state. Note that because the thickness of the central portion 40C protruding towards the excretion portion of the wearer is less and the rigidity is low, even when the central convex portion is supported by the absorber 40 positioned between the second curving means and the central curving means, the feeling of pressure caused to the wearer is low, and the deterioration in comfort when wearing the disposable diaper can be prevented.

Furthermore, as shown in FIG. 2, the absorber 40 has a first region A1 arranged posterior to the first elastic material, and a second region A2 arranged posterior to the first region A1 and having a rigidity different from the first region A1. The first region A1 is configured only by the first layer 41. In the second region A2, the ends in the widthwise direction of the first layer 41 are arranged. The ends in the widthwise direction of the first layer 41 arranged posterior to the first elastic material 48 are arranged to extend from inside the widthwise direction towards outside the widthwise direction in the posterior direction. Posterior to the ends of the first layer 41, the first layer 41 and the second layer are overlapping. Therefore, there is a difference in rigidity between the front and the back of the ends of the first layer 41, and the rigidity of the first region A1 differs from the rigidity of the second region A2. Thus, by providing the first region A1 and the second region A2 having different rigidities in the first elastic material 48, the effect of the deformation of the absorber 40 caused by the first elastic material 48 can be prevented from reaching up to the proximity of the hip portion where the second elastic material 49 is arranged.

That is, according to the disposable diaper 1, the absorption performance can be improved by bringing the absorber in close contact in the proximity of the excretion portion. Furthermore, the fitting at the back of the body can be improved while maintaining an appropriate gap at the front of the body, and the comfort when wearing the disposable diaper can be improved.

In the present embodiment, the absorber 40 has a double-layered structure including the first layer 41 and the second layer 42, but the absorber 40 of the worn article according to the present invention can have only a single layer, or three or more layers.

Modifications

Next, the configuration of the absorbers 40G, 40H, 40I, 40J, 40K, and 40L of the disposable diaper according to the first through sixth modification is explained with reference to drawings. Note that the same symbols have been used for the same portions as the disposable diaper 1 according to the aforementioned first embodiment, and mainly, the differences have been explained. FIG. 14 are plan views each illustrating an absorber of the disposable diaper according to the first through sixth modification. The absorber according to the first through fifth modification is configured only by the first layer.

As shown in FIG. 14 (*a*), the absorber 40G according to the first modification has a pair of first elastic materials 48 configuring the first curving means, and a pair of second elastic materials 49 configuring the lifting units. The configuration of the first elastic materials 48 and the second elastic materials 49 is the same as the first embodiment.

As shown in FIG. 14 (*b*), the absorber 40H according to the second modification is provided with a compression unit 75 in which the absorber 40 is compressed in the thickness direction between the first elastic materials 48 and the second elastic materials 49. The absorber 40H has a first region A1 arranged posterior to the first elastic materials 48, and a second region A2 arranged posterior to the first region A1 and having a rigidity higher than the first region A1. The second region A2 is the region in which the compression unit 75 is provided. The compression unit 75 is arranged posterior to the first elastic materials 48 to extend from inside the widthwise direction towards the outside, in the posterior direction. The second elastic materials 49 are arranged posterior to the compression unit 75.

By providing the first region A1 and the second region A2 having a rigidity different from that of the first region A1 posterior to the first elastic materials 48, the effect of the deformation of the absorber due to the first elastic materials 48 cannot easily reach posterior to the compression unit 75, and the effect of the deformation of the absorber due to the second elastic materials 49 cannot easily reach anterior to the compression unit 75. Therefore, the interaction between the deformation of the absorber due to the first elastic materials 48 and the deformation of the absorber due to the second elastic materials 48 can be prevented. Note that the compression unit 75 can be compressed in the thickness direction, for example, the compression unit 75 is formed by embossing.

As shown in FIG. 14 (*c*), the absorber 40I according to the third modification has a different outer shape than the absorber 40G according to the first modification. The absorber 40I has a pair of narrow units 40N, which have a narrow length in the widthwise direction, outside the lengthwise direction L corresponding to the crotch region S1. The first elastic materials 48 are arranged between the pair of narrow units 40N in the lengthwise direction L. A first region A1 and a second region A2 arranged posterior to the first region A1 and having a rigidity higher than the first region A1 are arranged posterior to the first elastic materials 48. The first region A1 is a recessed region inside the widthwise direction of the absorber, and the second region A2 is a region in which the ends in the widthwise direction of the absorber are arranged.

Thus, by providing the narrow units 40N posterior to the crotch region S1 in which the first elastic materials 48 are provided, and by providing the first region A1 and the second region A2, the extension of the convex portion formed by the first elastic materials 48 in the crosswise direction from the crotch region S1 can be prevented. Therefore, for example, in the hip portion that is positioned outside the crosswise direction with respect to the crotch portion, the worn article can easily be arranged along the body, and the fitting can be improved further.

In an absorber 40J according to the fourth modification, as shown in FIG. 14 (*d*), a central elastic material 44 configuring the central curving means is provided anterior to the first elastic materials 48. The central elastic material 44 and the first elastic materials 48 are arranged in the widthwise direction such that there is no overlapping. By providing the central elastic material 44, the central portion of the absorber 40 is formed in a convex shape towards the wearer, and the adhesion between the excretion portion and the absorber 40 can be improved.

As shown in FIG. 14 (*e*), in the absorber 40K according to the fifth modification, the second elastic materials 49 are extended anterior and posterior to the first elastic materials 48 and arranged. The second elastic materials 49 are arranged such that the extension stress becomes lesser than that of the first elastic materials 48 in the state prior to deformation. According to such a configuration, the ends outside the widthwise direction of the absorber 40 are lifted up towards the wearer, and the leakage of the bodily fluid from the sides of the absorber can be prevented.

As shown in FIG. 14 (*f*), the absorber 40L according to the sixth modification is configured by the first layer 41 and the second layer 42. The first layer 41 of the absorber 40L has a narrow unit that is recessed towards the center of the widthwise direction W, and a wide unit having a width longer than the narrow unit. The narrow unit is arranged in the crotch region S1. The side ends of the narrow unit and the side ends of the wide unit are connected by a curved line, and the first layer 41 has a planar shape in the form of an hourglass.

The second elastic materials 49 are provided in the portion where the first layer 41 and the second layer 42 overlap. The second layer 42 has a rectangular shape, which includes the lengthwise direction L and the widthwise direction W. The first elastic materials 48 are provided only in the second layer 42. The first region A1 posterior to the first elastic materials 48 is configured only by the second layer 42. The second region A2 in which the ends outside the widthwise direction of the first layer 41 are arranged is provided posterior to the first region A1. The configuration is such that the thickness and rigidity of the absorber is different in the first region A1 and the second region A2. Note that in the present embodiment, the lifting units are arranged across the portion in which the first layer and the second layer overlap, and the portion including only the second layer. However, the lifting units can be configured to be arranged only in the portion where the first layer and the second layer overlap, for example. Furthermore, the first region or the second region can be configured to be provided by forming slits in the absorber in the form of apertures.

As shown in FIG. 14 (g), in the absorber 40M according to the seventh modification, the elastic materials configuring the first curving means and the elastic materials configuring the lifting units are configured by the same third elastic materials 51. The third elastic materials 51 have a first elastic portion 51a configuring the first curving means, a second elastic portion 51b configuring the lifting units, and a third elastic portion 51c between the first elastic portion 51a and the second elastic portion 51b. The third elastic portion 51c extends from inside the widthwise direction towards the outside in the posterior direction, and deforms the absorber in the inner direction facing the wearer. Because of the deformation of the absorber due to the third elastic portion 51c, the effect of the deformation of the absorber due to the first elastic portion 51a cannot easily reach posterior to the third elastic portion 51c, and the effect of the deformation of the absorber due to the second elastic portion 51b cannot easily reach anterior to the third elastic portion 51c.

Note that the extension stress of the third elastic portion 51c is configured to be more than the extension stress of the first elastic portion 51a. The extension magnitude of the third elastic portion 51c is desired to be in the range of 1.5 times to 3.5 times. By thus providing the elastic materials configuring the first curving means and the elastic materials configuring the lifting unit as one part, the number of components is reduced thereby reducing the manufacturing cost and improving the production efficiency.

Other Embodiments

As mentioned above, although the content of the present invention was disclosed through the embodiments of the present invention, the descriptions and drawings that form a part of this disclosure are not to be considered as limitation to the present invention. From this disclosure, a variety of alternate embodiments, examples, and applicable techniques will become apparent to one skilled in the art.

For example, in the above embodiment, a pant-type disposable diaper was explained, however, the present invention is not limited thereto, and can be applied to an open-type disposable diaper, incontinence pad, and sanitary napkin.

In the aforementioned embodiment, the absorber was configured to be curved by using slits, elastic materials, and boundary portions where the rigidity changes, however, the absorber can also be configured to be curved by reducing the thickness of the absorber and by performing embossing in the absorber.

As described above, needless to say, the present invention includes various embodiments and the like not described here. Therefore, the technical range of the present invention is to be defined only by the inventive specific matter according to the adequate claims from the above description.

The entire contents of Japanese Patent Application No. 2011-050869 (filed on Mar. 8, 2011) are incorporated in the present specification by reference.

INDUSTRIAL APPLICABILITY

According to the present invention, because the back ends of the lifting units are positioned posterior to the back ends of the curving means, the effect of curving of the absorber in the inner direction due to the curving means is reduced in the region posterior to the back ends of the curving means, and only the deformation in the inner direction caused by the lifting units can act easily. In the region posterior to the back ends of the curving means, the absorber is deformed due to the lifting units so as to curve towards the wearer. Because the curving means are not provided between the lifting units in the widthwise direction, the absorber does not get deformed towards the wearer. Therefore, the absorber curves stably in the proximity of the hip portion. As a result, by fitting the absorber in the hip portion of the wearer in the proximity of the hip portion, the deterioration in comfort when wearing the disposable diaper and the occurrence of leakage can be prevented.

The invention claimed is:

1. A disposable wearing article, comprising:
an absorber having
a lengthwise direction configured to extend to a front of a body of a wearer and a back of the body of the wearer,
a widthwise direction perpendicular to the lengthwise direction,
an inner direction configured to face the wearer,
an outer direction opposite to the inner direction,
a crotch region configured to be in contact with a crotch portion of the wearer,
a front region arranged anterior to the crotch region in the lengthwise direction, and
a back region arranged posterior to the crotch region in the lengthwise direction and configured to be in contact with a hip portion of the wearer;
a pair of curving members provided in the crotch region and extending along the lengthwise direction to enable the absorber to curve in a convex shape in the inner direction; and
a pair of lifting units provided outside the curving members in the widthwise direction and extending along the lengthwise direction to enable the absorber to be lifted up in the inner direction in the back region,
wherein
back ends of the curving members are positioned anterior to back ends of the lifting units in the lengthwise direction, and
the curving members and the lifting units are arranged to overlap the absorber.

2. The disposable wearing article according to claim 1, wherein
the curving members are first elastic materials arranged along the lengthwise direction, and
the lifting units are second elastic materials arranged along the lengthwise direction.

3. The disposable wearing article according to claim 2, wherein
at least a part of the curving members overlaps a portion of the lifting units in the widthwise direction, and
an extension stress of said at least the part of the curving members is more than an extension stress of the portion of the lifting units.

4. The disposable wearing article according to claim 2, further comprising:
a leg hole elastic material configured to extend along a leg portion of the wearer and located in the front region and the back region,
wherein
the leg hole elastic material includes a back leg hole elastic material in the back region, and
a first elongated line extending from an end of the back leg hole elastic material on a first elastic material side to the first elastic material side along the back leg hole elastic material, or the back leg hole elastic material intersects a second elongated line extending posteriorly from the back end of the first elastic material along the first elastic material, or the first elastic material.

5. The disposable wearing article according to claim 4, wherein
the leg hole elastic material further includes a front leg hole elastic material in the front region,
a third elongated line extending from an end of the front leg hole elastic material on the first elastic material side to the first elastic material side along the front leg hole elastic material, or the front leg hole elastic material intersects a fourth elongated line extending anteriorly from the front end of the first elastic material along the first elastic material, or the first elastic material.

6. The disposable wearing article according to claim 1, wherein
the lifting units have front ends opposing the back ends in the lengthwise direction,
the back ends of the curving members are positioned posterior to the front ends of the lifting units in the lengthwise direction, and
a distance in the lengthwise direction between the back ends of the curving members and the front ends of the lifting units is 20 mm or less.

7. The disposable wearing article according to claim 1, wherein
the lifting units have front ends opposing the back ends in the lengthwise direction,
the back ends of the curving members are positioned anterior to the front ends of the lifting units in the lengthwise direction.

8. The disposable wearing article according to claim 1, wherein the absorber has
a first region arranged posterior to the curving members in the lengthwise direction, and
a second region arranged posterior to the first region in the lengthwise direction and having a different rigidity than the first region.

9. The disposable wearing article according to claim 8, wherein the second region is arranged to extend in the lengthwise direction from inside in the widthwise direction towards outside in the widthwise direction.

10. The disposable wearing article according to claim 1, further comprising:
a central curving member located between the pair of curving members in the widthwise direction and extending along the lengthwise direction to enable the absorber to curve in the convex shape in the inner direction,
wherein the absorber has a top surface configured to be in contact with the crotch portion of the wearer when the absorber is curved in the convex shape in the inner direction.

11. The disposable wearing article according to claim 10, wherein the back ends of the curving members are positioned, in the lengthwise direction, anterior to a back end of the central curving member.

12. The disposable wearing article according to claim 1, wherein
the pair of curving members is arranged to overlap the absorber in the lengthwise direction, and
the pair of lifting units is arranged to overlap the absorber in a thickness direction of the disposable wearing article.

13. The disposable wearing article according to claim 1, wherein an entirety of the pair of curving members is located between the pair of lifting units in the widthwise direction.

14. The disposable wearing article according to claim 1, wherein
the absorber has a pair of side slits extending in the lengthwise direction,
the pair of curving members overlaps the pair of side slits, respectively, in a thickness direction of the disposable wearing article, and
the pair of lifting units are located outside the pair of side slits in the widthwise direction.

15. A disposable wearing article, comprising:
an absorber having
a lengthwise direction configured to extend to a front of a body of a wearer and a back of the body of the wearer,
a widthwise direction perpendicular to the lengthwise direction,
an inner direction configured to face the wearer,
an outer direction opposite to the inner direction,
a crotch region configured to be in contact with a crotch portion of the wearer, and
a back region arranged posterior to the crotch region in the lengthwise direction and configured to be in contact with a hip portion of the wearer;
a pair of first elastic materials in the crotch region and extending along the lengthwise direction;
a pair of second elastic materials outside the first elastic materials in the widthwise direction and extending along the lengthwise direction in the back region,
wherein
back ends of the first elastic materials are positioned anterior to back ends of the second elastic materials in the lengthwise direction,
at least a part of the first elastic materials overlaps a portion of the second elastic materials in the widthwise direction, and
an extension stress of said at least the part of the first elastic materials is more than an extension stress of the portion of the second elastic materials.

16. A disposable wearing article, comprising:
an absorber having a crosswise direction configured to extend to a front of a body of a wearer and a back of the body of the wearer, a widthwise direction perpendicular to the crosswise direction, an inner direction configured to face the wearer, and an outer direction opposite to the inner direction, the absorber having
a crotch region configured to be in contact with a crotch portion of the wearer,
a front region arranged anterior to the crotch region, and
a back region arranged posterior to the crotch region and configured to be in contact with a hip portion of the wearer;
wherein
in the crotch region, a pair of curving means are provided along the crosswise direction so as to enable the absorber to curve in a convex shape in the inner direction,
outside the widthwise direction of the curving means, a pair of lifting units are provided along the crosswise direction so as to enable the absorber to be lifted up in the inner direction in the back region,
back ends of the curving means are positioned anterior to back ends of the lifting units,
the back ends of the curving means are positioned posterior to front ends of the lifting units, and
a distance in the crosswise direction between the back ends of the curving means and the front ends of the lifting units is 20 mm or less.

* * * * *